United States Patent [19]

Iwao et al.

[11] 4,410,542
[45] Oct. 18, 1983

[54] DISULFIDE COMPOUNDS

[75] Inventors: Jun-ichi Iwao, Takarazuka; Masayuki Oya, Ibaraki; Tadashi Iso, Tondabayashi, all of Japan

[73] Assignee: Santen Pharmaceutical Co., Ltd., Osaka, Japan

[21] Appl. No.: 186,271

[22] Filed: Sep. 11, 1980

Related U.S. Application Data

[62] Division of Ser. No. 104,970, Dec. 18, 1979, Pat. No. 4,347,371.

[30] Foreign Application Priority Data

Dec. 30, 1978 [JP] Japan ................................ 53-163964
Jan. 29, 1979 [JP] Japan ................................ 54-009392
Mar. 17, 1979 [JP] Japan ................................ 54-031334
Jun. 26, 1979 [JP] Japan ................................ 54-081043
Jul. 3, 1979 [JP] Japan ................................ 54-084837

[51] Int. Cl.³ .................... C07D 207/16; A61K 31/40
[52] U.S. Cl. ................... 424/274; 548/200; 548/201; 548/517; 548/518; 548/533; 548/537; 424/263; 424/270; 546/280; 546/281
[58] Field of Search ......... 260/326.2, 326.46, 326.47, 260/326.36, 326.25, 326.42; 424/274, 263; 548/518, 517, 533, 537

[56] References Cited

U.S. PATENT DOCUMENTS 4,046,889  9/1977  Ondetti et al. .................. 260/326.2
4,105,776  8/1978  Ondetti et al. .................. 260/326.25
4,154,935  5/1979  Ondetti et al. .................. 260/326.25
4,241,076 12/1980  Ondetti et al. .................. 260/326.25
4,248,883  2/1981  Sawayama et al. ............. 260/326.25
4,284,624  8/1981  Natarajan et al. ............. 260/326.25

FOREIGN PATENT DOCUMENTS 2703828  8/1977  Fed. Rep. of Germany .

OTHER PUBLICATIONS

Chem. Abstract, vol. 88, 1978, 88: 7376c.

*Primary Examiner*—Mary C. Lee
*Attorney, Agent, or Firm*—Frishauf, Holtz, Goodman & Woodward

[57] ABSTRACT

Disulfide compounds which have the general formula

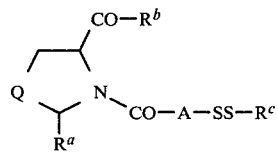

and salts thereof used for reducing blood pressure and for preventing or relieving diabetic complications, processes for manufacturing thereof, compositions comprising them and pharmaceutically acceptable excipients, and administering methods are mentioned.

14 Claims, No Drawings

DISULFIDE COMPOUNDS

This is a division of application Ser. No. 104,970 filed Dec. 18, 1979, now U.S. Pat. No. 4,347,371.

DETAILED DESCRIPTION OF THE INVENTION

This invention relates to disulfide compounds which have the general formula

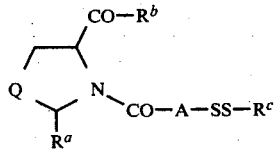

[I]

and salts thereof used for reducing blood pressure and for preventing or relieving diabetic complications, wherein Q is sulfur or methylene;
$R^a$ is $R^1$, $R^4$, $R^7$, $R^{10}$, $R^{13}$ or $R^{16}$;
$R^b$ is $R^2$, $R^5$, $R^8$, $R^{11}$, $R^{14}$ or $R^{17}$;
$R^c$ is $R^3$, $R^6$, $R^9$, $R^{12}$, $R^{15}$ or $R^{18}$;
A is alkylene having 1 to 3 carbon atoms, preferably —CH$_2$—, —CH(CH$_3$)—, —(CH$_2$)$_2$—, —CH(CH$_3$)CH$_2$— or —(CH$_2$)$_3$—;

$R^1$ is acylmercapto-lower alkyl, alkyl having 8 to 20 carbon atoms, alkenyl having 2 to 20 carbon atoms, cycloalkyl, aralkyl, phenyl, furyl, thienyl, pyridyl, naphthyl, substituted cycloalkyl, substituted aralkyl, substituted phenyl, substituted furyl, substituted thienyl, substituted pyridyl or substituted naphthyl wherein the substituents are 1 to 3 groups independently selected from lower alkyl, hydroxy, lower alkoxy, lower alkylenedioxy, acyloxy, acylmercapto, halogen, nitro, amino, lower alkylamino, acylamino, carboxy, sulfamoyl and lower alkylaminosulfonyl, preferably, 2,6-dimethyl-5-heptenyl, cyclohexyl, S-acetyl-2-mercaptoethyl, benzyl, phenyl, 4-methylphenyl, 2-chlorophenyl, 4-chlorophenyl, 2,4-dichlorophenyl, 4-fluorophenyl, 2-nitrophenyl, 3-nitrophenyl, 4-nitrophenyl, 4-dimethylaminophenyl, 4-acetaminophenyl, 4-benzyloxycarbonylaminophenyl, 2-carboxyphenyl, 2-hydroxyphenyl, 3-hydroxyphenyl, 3-benzoxyphenyl, 4-hydroxyphenyl, 4-benzyloxycarbonyloxyphenyl, 3,4-dihydroxyphenyl, 5-chloro-2-hydroxyphenyl, 2-methoxyphenyl, 4-methoxyphenyl, 3,4-dimethoxyphenyl, 3,4,5-trimethoxyphenyl, 2-hydroxy-3-methoxyphenyl, 2-hydroxy-4-methoxyphenyl, 4-hydroxy-3-methoxyphenyl, 3-methoxy-4-pivaloyloxyphenyl, 3,4-methylenedioxyphenyl, 2-acetoxyphenyl, 1-naphthyl, 2-furyl, 2-(5-methyl)furyl, 2-thienyl, 3-pyridyl, 4-pyridyl or 2-hydroxy-5-sulfamoylphenyl;

$R^2$ is hydroxy, lower alkoxy, amino, phenoxy, substituted lower alkoxy wherein the substituent is hydroxy, succinimido, maleimido, phthalimido or lower alkanoyloxy or substituted phenoxy wherein the substituent is hydroxy, lower alkoxy or halogen, preferably hydroxy, ethoxy, butoxy, amino, succinimidomethoxy, 1-succinimidoethoxy, phthalimidomethoxy, 2-phthalimidoethoxy, pivaloyloxymethoxy or 1-pivaloyloxyethoxy;

$R^3$ is alkyl having 1 to 10 carbon atoms, phenyl, lower alkenyl, aralkyl, tetrahydrofuryl-lower alkyl, $R^{19}$,

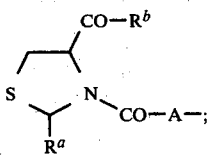

substituted lower alkyl or substituted phenyl wherein the substituents are 1 to 2 groups independently selected from lower alkyl, hydroxy, lower alkoxy, acyloxy, amino, lower alkylamino, acylamino, carboxy and carbamoyl, preferably methyl, ethyl, n-propyl, n-octyl, allyl, 2-hydroxyethyl, tetrahydrofurfuryl, benzyl,

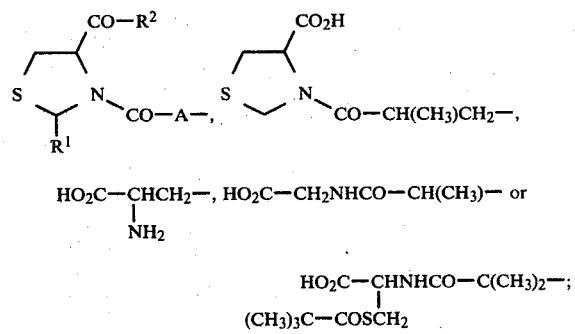

$R^4$ is phenyl, substituted phenyl wherein the substituent is lower alkyl, hydroxy, alkoxy or acyloxy, preferably phenyl, 2-hydroxyphenyl, 4-hydroxyphenyl or 2-acetoxyphenyl;

$R^5$ is hydroxy, lower alkoxy, amino, phenoxy, substituted lower alkoxy wherein the substituent is phthalimido or lower alkanoyloxy, preferably hydroxy or pivaloyloxymethoxy;

$R^6$ is alkyl having 1 to 10 carbon atoms, lower alkenyl, tetrahydrofuryl-lower alkyl,

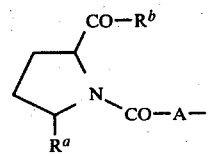

or substituted lower alkyl wherein the substituents are 1 to 2 groups independently selected from carboxy, carbamoyl, amino and acylamino, preferably n-propyl, allyl, tetrahydrofurfuryl or

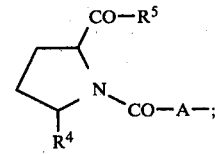

$R^7$, $R^{10}$, $R^{13}$ and $R^{16}$ each is hydrogen or lower alkyl;
$R^8$ is hydroxy or lower alkoxy, preferably hydroxy or ethoxy;
$R^9$ is alkyl having 1 to 10 carbon atoms, lower alkenyl, tetrahydrofuryl-lower alkyl, phenyl, aralkyl, $R^{19}$, substituted lower alkyl or substituted phenyl wherein the substituents are 1 to 2 groups independently selected from lower alkyl, hydroxy, lower alkoxy, acyloxy, amino, lower alkylamino, acylamino, carboxy and carbamoyl, preferably n-propyl, n-octyl, allyl or tetrahydrofurfuryl;

$R^{11}$ is amino, phenoxy or substituted lower alkoxy wherein the substituent is hydroxy, succinimido, maleimido, phthalimido or lower alkanoyloxy, preferably pivaloyloxymethoxy or phthalimidomethoxyl;

$R^{12}$ is alkyl having 1 to 10 carbon atoms, lower alkenyl, tetrahydrofuryl-lower alkyl or

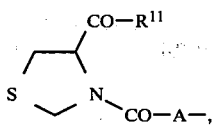

preferably n-propyl, tetrahydrofurfuryl or

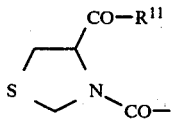

$R^{14}$ is hydroxy, amino or lower alkoxy, preferably hydroxy or ethoxy;

$R^{15}$ is alkyl having 8 to 10 carbon atoms, lower alkenyl, tetrahydrofuryl-lower alkyl, aralkyl, substituted lower alkyl wherein the substituent is carboxy or carbamoyl, preferably n-octyl, allyl or tetrahydrofurfuryl;

$R^{17}$ is phenoxy or substituted lower alkoxy wherein the substituent is hydroxy, succinimido, maleimido, phthalimido or lower alkanoyloxy, preferably pivaloyloxymethoxy or 2-phthalimidoethoxy;

$R^{18}$ is alkyl having 1 to 10 carbon atoms, lower alkenyl, tetrahydrofuryl-lower alkyl or

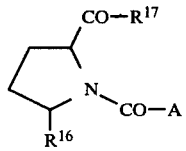

preferably tetrahydrofurfuryl or

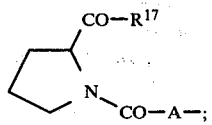

$R^{19}$ is

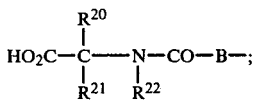

B is lower alkylene;
$R^{20}$ and $R^{22}$ each is hydrogen or lower alkyl;
$R^{21}$ is hydrogen, lower alkyl or acylmercapto-lower alkyl; acyl is lower alkanoyl, benzoyl or benzyloxycarbonyl; and salts thereof, said lower alkyl, lower alkoxy, lower alkylenedioxy, lower alkenyl, lower alkylene and lower alkanoyl groups having 1 to 7 carbon atoms. The same shall be applied hereinafter.

The compounds [I] of this invention are disulfide compounds and these esters or these amides of mercaptoacylamino acids which are effective as angiotensin I-converting enzyme inhibitors for symptom of hypertension. They release mercaptoacylamino acids which are already proved to be efficacious by enzymatic and/or chemical cleavage of disulfide bond and by enzymatic hydrolysis of their esters or amides when administered to man and animal. Mercaptoalcylamino acids are generally susceptible to inactivation by oxidation in vivo and decomposition in process of manufacturing themselves or their preparations or with the elapse of time because of the compounds having chemically and biologically active sulfhydryl group. Accordingly, problems are that their activity decrease and effective time is shortened. Our strenuous investigation has been undertaken in order to disolve the problems. An initial attempt of protection by acylation of sulfhydryl group resulted in maintaining duration of the activity to some extent. Our continuous studies were allowed to achieve the long-lasting effect in vivo by conversion of sulfhydryl group into disulfide group. In addition thereto, these disulfide compounds did not give a lowering of the potencies and an evolution of bad odors by decomposition in process of preparation or with the elapse of time. Formation of an ester or an amide of the disulfide compound led to not only prolongation of the duration but also improvement of absorption characteristics as a result of increase of lipophilicity.

On the other hand, we have found tht the compounds [I] of this invention were effective on preventing or relieving diabetic complications beyond our expectation.

In diabetic patients, high lebels of hexoses (e.g., glucose, galactose, etc.) in blood lead to the accumulation of sugar alcohols (e.g., sorbitol, galactitol, etc.) in tissues. It is known that this accumulation causes the swelling of cells to induce complications of diabetic cataract, diabetic retinopathy, diabetic nephropathy, diabetic neuropathy, etc. [R. Quan-Ma et al., Biochem. Biophys. Res. Comm., 22, 492 (1966)]. For example, R. Gitzelman et al. have presented that cataract is caused by the accumulation of sugar alcohols [Exptl. Eye Res., 6, 1 (1967)]. A report of Kinoshita et al. has demonstrated that aldose reductase which reduced aldoses to the corresponding sugar alcohols was involved in the initiation of these diabetic complications and that effective inhibitors of aldose reductase were useful [Jpn. J. Ophthalmol., 20, 399 (1976)]. On the basis of the above information, aldose reductase inhibition of the compounds [I] of this invention was tested. The results of the examinations demonstrated that these compounds were useful as drugs for therapy or prophylaxis of the diabetic complications because of their strong aldose reductase inhibition.

The compounds [I] of this invention can be prepared by the following methods.

(i) A disulfide compound of this invention represented by the formula

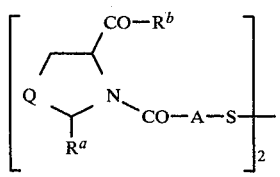 [II]

is yielded by oxidation of a compound of the formula

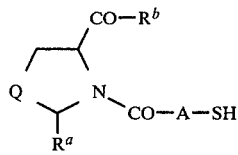 [III]

in the presence or the absence of base (e.g., sodium hydroxide, sodium bicarbonate, etc.) with air or one equivalent of oxidant (e.g., iodine, ferric chloride, hydrogen peroxide, sodium persulfate, etc.) in water, methanol, ethanol, acetic acid or solution mixed them at a temperature in the range of 5° to 60° C.

(ii) A disulfide compound of the formula [II] is yielded by reaction of a compound of the formula [III] with a compound of the formula

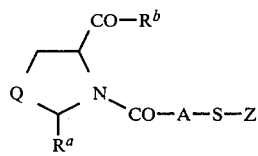 [IV]

wherein
Z is —SO₃E, —SCN, —CN, —NO, —SCO₂R²⁴ or —SO₂R²⁵;
R²⁴ is CH₃, C₂H₅, (CH₃)₃C or C₆H₅CH₂;
R²⁵ is CH₃, C₂H₅, C₆H₅, p—CH₃C₆H₄;
E is alkali metal;
same hereinafter,
in water or an alcohol (e.g., methanol, ethanol, etc.) containing an alkali (e.g., sodium hydroxide, sodium carbonate, etc.) or in organic solvent (e.g., methanol, ethanol, ethyl acetate, ether, tetrahydrofuran, chloroform, carbon tetrachloride, solvent mixed them, etc.), if necessary, containing triethylamine at a temperature in the range of −30° to 40° C.

A compound of the formula [IV] is obtained by reaction of a compound of the formula [III] with a slight excess of thiocyanogen, cyanogen, cyanogen chloride, dinitrogen tetraoxide, carboalkoxysulfenyl chloride, p-toluensulfonyl chloride or benzenesulfonyl chloride in the above solvent in the same temperature range, if necessary, in the presence of triethylamine or the above alkali, and utilized to next reaction without isolation.

A compound of the formula [IV], wherein Z is —SO₃E is obtained by reaction of a compound of the formula

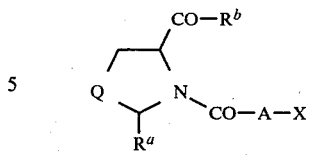 [V]

wherein
X is halogen;
same hereinafter,
with alkali metal thiosulfate in an alcohol (e.g., methanol, ethanol, etc.) containing water at a temperature from room temperature to reflux one. This compound of the formula [IV] is heated in an aqueous alkali (e.g., potassium hydroxide, sodium hydroxide, etc.) solution to yield a disulfide compound of the formula [II].

A compound of the formula [IV], wherein Z is —SO₂R²⁵, can also be obtained by reaction of a compound of the formula [V] with a alkali metal thiosulfonate of the formula

R²⁵SO₂SE    [VI]

prepared from a corresponding alkyl- or arylsulfonyl chloride and alkali metal sulfide, in an alcohol (e.g., methanol, ethanol, etc.) adding a proper amount of water, if necessary, in the presence of an alkali (e.g., sodium hydroxide, potassium hydroxide, etc.) at a temperature in the range of 20° to 80° C.

(iii) A disulfide compound of the formula [II] is yielded by acylation of a compound of the formula

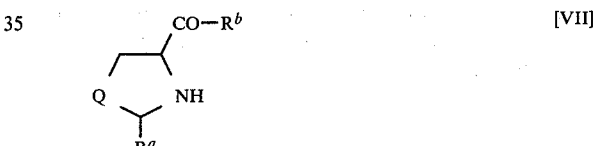 [VII]

with a dithiodialkanoic acid or a dithiodialkanoyl dihalide of the formula

[Y—CO—A—S—]₂    [VIII]

wherein
Y is hydroxy or halogen;
same hereinafter,
under the following conditions.

When Y in the formula [VIII] is hydroxy, a compound of the formula [VII] is acylated with half the molar quantity of a mixed anhydride of dithiodialkanoic acid in an anhydrous organic solvent (e.g., dichloromethane, tetrahydrofuran, dioxane, acetonitrile, ethyl acetate, dimethylformamide, pyridine, etc.) or an organic solvent (e.g., tetrahydrofuran, dioxane, acetonitrile, dimethylformamide, etc.) adding a proper amount of water, if necessary, in the presence of an alkali or an organic base (e.g., sodium hydroxide, potassium carbonate, sodium bicarbonate, triethylamine, N-methylmorphorine, dicyclohexylamine, etc.) at a temperature in the range of −20° to 50° C.

The mixed anhydride is prepared from a dithiodialkanoic acid of the formula [VIII], wherein Y is hydroxy, and double the molar quantity of an alkyl chloroformate (e.g., ethyl chloroformate, isobutyl chloroformate, etc.) in the presence of the above organic base in the above anhydrous organic solvent at a temperature in the range of −20° to −5° C.

When Y in the formula [VIII] is hydroxy and a compound of the formula [VII] have no carbonyl group, the compound of the formula [VII] is acylated with half the molar quantity of a dithiodialkanoic acid of the formula [VIII] and N,N'-dicyclohexylcarbodiimide (DCC) in the above organic solvent (single or mixed) at a temperature from 0° C. to reflux temperature.

When Y in the formula [VIII] is halogen, a compound of the formula [VII] is acylated with half the molar quantity of a dithiodialkanoyl dihalide of the formula [VIII] in the presence of the said alkali or organic base in water, anhydrous organic solvent such as acetone, ether, tetrahydrofuran, chloroform, dichloromethane, dioxane, acetonitrile, ethyl acetate, N,N-dimethylformamide, etc. (single or mixed) or water adding a proper amount of the organic solvent at a temperature in the range of 0° to 50° C., or acylated with the halide in triethylamine or pyridine at a temperature from 0° C. to room temperature.

This acylation reaction is also achieved by the use of a general coupling agent such as N-ethoxycarbonyl-2-ethoxy-1,2-dihydroquinoline (EEDQ), ethoxyacetylene, carbonyldiimidazole (CDI), N-ethyl-5-phenylisoxazolium-3'-sulfonate (Woodward's Reagent K), diphenylphosphoryl azide (DPPA), 1-ethyl-3-(3-dimethylaminopropyl)carbodiimide hydrochloride (Water Soluble Carbodiimide), etc., for peptide synthesis as well as the above so-called mixed anhydride method, DCC method and Schotten-Baumann method.

(iv) A disulfide compound of the formula [II] is yielded by acylation of a compound of the formula [VII] with a haloalkanoic acid or a haloalkanoyl halide of the formula

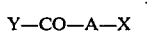
Y—CO—A—X            [IX]

under the same condition as described in the method (iii), and then treatment of the resulting acylated compound of the formula [V] with sodium disulfide in water, an alcohol (e.g., methanol, ethanol, etc.) or an alcohol adding water at a temperature from 20° C. to reflux temperature.

(v) A disulfide compound of this invention represented by the formula

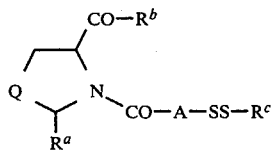
[I]

is yielded by reaction of a compound of the formula [III] with a compound of the formula

R$^c$—S—Z            [X]

under the same condition as described in the method (ii), or reaction of a compound of the formula [III] with a compound of the formula [X], wherein Z is imido such as phthalimido, succinimido, etc., in an organic solvent (e.g., methanol, ethanol, ethyl acetate, etc.) or an alcohol (e.g., methanol, ethanol, etc.) adding water at reflux temperature.

The compound of the formula [X], wherein Z is imido, is obtained by halogenating a compound of the formula

R$^c$—SH            [XI]

or a compound of the formula
[R$^c$—S─]$_2$            [XII]

in an inert organic solvent (e.g., hexane, dichloromethane, chloroform, carbon tetrachloride, 1,2-dichloroethane, etc.) at ca. 0° C., and then treating the resulting sulfenyl halide with alkali metal or triethylamine salt of an imide such as phthalimide, succinimide, etc., in the same solvent or N,N-dimethylformamide at a temperature from 0° C. to room temperature.

Similarly, a disulfide compound of the formula [I] can be prepared from a compound of the formula [III] and a compound of the formula [X] wherein Z is leaving group such as X, R$^c$—SO—, R$^c$—SO$_2$—, etc.

(vi) A disulfide compound of the formula [I] is yielded by reaction of a compound of the formula [IV] with a compound of the formula [XI] under the same condition as described in the method (ii).

(vii) A disulfide compound of the formula [I] is yielded by exchange reaction of a compound of the formula [III] with a compound of the formula [XII] or exchange reaction of a disulfide of the formula [II] with a compound of the formula [XI] in water, an alcohol (e.g., methanol, ethanol, etc.) or an alcohol adding water at pH 5–9, if necessary, added an alkali (e.g., sodium hydroxide, potassium bicarbonate, etc.) at room temperature.

(viii) A disulfide compound of the formula [I], wherein R$^c$ is —A—CO$_2$H, is yielded by reaction of a compound of the formula [VII] with dithiodialkanoyl dihalide of the formula [VIII], wherein Y is halogen, or a dithiodialkanoic anhydride of the formula

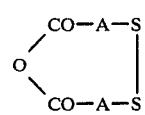
[XIII]

under a condition similar to the method (iii), and then by treatment with acidic aqueous solution (e.g., N aqueous hydrochloric acid solution, etc.).

(ix) A disulfide ester of this invention represented by the formula

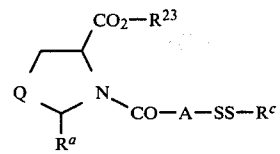
[XIV]

wherein
R$^{23}$ is lower alkyl, phenyl, substituted lower alkyl wherein the substituent is hydroxy, succinimido, maleimido, phthalimido or lower alkanoyloxy or substituted phenyl wherein the substituent is hydroxy, lower alkoxy or halogen;
same hereinafter,
is yielded by esterification of a compound of the formula

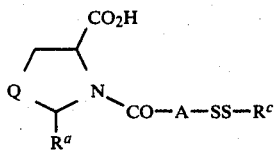

with a halide or an alcohol of the formula $R^{23}$—Y  [XVI]

under the following conditions.

When Y in the formula [XVI] is hydroxy, the compound of the formula [XV] is esterified in the presence of acid catalyst (e.g., hydrogen chloride, concentrated sulfuric acid, p-toluenesulfonic acid, trifluoroacetic acid, boron trifluoride, etc.) in the alcohol of the formula [XVI], if necessary, adding azeotropic solvent (e.g., benzene, chloroform, 1,2-dichloroethane, etc.) at a temperature from room temperature to reflux one.

When Y in the formula [XVI] is halogen, the compound of the formula [XV] is esterified in the presence of an alkali or an organic base (e.g., sodium carbonate, potassium carbonate, sodium bicarbonate, sodium hydroxide, triethylamine, etc.) at a temperature from room temperature to 100° C. in an anhydrous organic solvent (e.g., acetone, N,N-dimethylformamide, etc.), or esterified in the presence of an alkali or an alkoxide (e.g., sodium hydroxide, potassium hydroxide, sodium methoxide, potassium ethoxide, potassium tert-butoxide, etc.) in an anhydrous alcohol (e.g., methanol, ethanol, isopropanol, tert-butanol, etc.) or anhydrous N,N-dimethylformamide at a temperature from room temperature to reflux one.

(x) An acyl compound of this invention represented by the formula [I], wherein $R^a$ is phenyl substituted by acyloxy or acylamino, is yielded by acylation of a compound of the formula [I], wherein $R^a$ is phenyl substituted by hydroxy or amino, with an acid anhydride or an acyl halide in the presence of an alkali or an organic base (e.g., sodium hydroxide, potassium hydroxide, sodium carbonate, sodium bicarbonate, triethylamine, etc.) in water, an organic solvent (e.g., acetone, tetrahydrofuran, benzene, dichloromethane, etc.) or water adding the organic solvent at a temperature in the range of 0° to 50° C.

This acylation reaction can also be achieved in the presence of a catalyst (e.g., concentrated sulfuric acid, fused zinc chloride, an anhydrous sodium salt of the acid, etc.) in the acid anhydride or the acyl halide at a temperature from room temperature to 80° C., if necessary, cooled at 0° C., or achieved with the acid anhydride or the acyl halide in pyridine or triethylamine at a temperature from ca 5° C. to room temperature, if necessary, heated until reflux temperature.

The compounds of the formula [I] prepared by the above methods can form the conventional salts to be generally used as medicine such as sodium salt, potassium salt, calcium salt, aluminum salt, ammonium salt, diethylamine salt, triethanolamine salt, etc.

The compounds of the formula [I] have the stereoisomers which are within the limit of this invention, because they have one or more asymmetric carbon atoms.

Typical examples are shown below, although this invention is not limited to these examples.

EXAMPLE 1

(4R,4'R)-3,3'-[3,3'-Dithiobis[propanoyl)]bis[2-(2-hydroxyphenyl)-4-thiazolidinecarboxylic acid] (Compound 1)

To a stirred solution of 3.1 g of (4R)-2-(2-hydroxyphenyl)-3-(3-mercaptopropanoyl)-4-thiazolidinecarboxylic acid in 80 ml of methanol, 101 ml of 0.1 N aqueous potassium triiodide solution is added dropwise. The resulting mixture is continuously stirred for 10 min at room temperature, and then methanol is removed in vacuo. The separated crystals of the titled compound are filtered. The yield is 2.9 g (93%).

The compounds shown in Table I, II and III are prepared by the same procedure as described above. Similarly the compounds shown below are prepared by this method.

(4R,4'R)-3,3'-[3,3'-Dithiobis[(2S)-2-methylpropanoyl]]bis(2-benzyl-4-thiazolidinecarboxylic acid) from (4R)-2-benzyl-3-[(2S)-3-mercapto-2-methylpropanoyl]-4-thiazolidinecarboxylic acid: amorph.; $[\alpha]_D^{25}$ −151.0° (c=1.0, MeOH).

(4R,4'R)-3,3'-[3,3'-Dithiobis(propanoyl)]bis[2-(2-chlorophenyl)-4-thiazolidinecarboxylic acid] from (4R)-2-(2-chlorophenyl)-3-(3-mercaptopropanoyl)-4-thiazolidinecarboxylic acid: mp 133°–134° C.; $[\alpha]_D^{26}$ −64.6° (c=1.0, MeOH).

(4R,4'R)-3,3'-[3,3'-Dithiobis(propanoyl)]bis[2-(4-chlorophenyl)-4-thiazolidinecarboxylic acid] from (4R)-2-(4-chlorophenyl)-3-(3-mercaptopropanoyl)-4-thiazolidinecarboxylic acid: amorph.; $[\alpha]_D^{26}$ +77.1° (c=1.0, MeOH).

(4R,4'R)-3,3'-[2,2'-Dithiobis(acetyl)]bis[2-(2,4-dichlorophenyl)-4-thiazolidinecarboxylic acid] from (4R)-2-(2,4-dichlorophenyl)-3-(2-mercaptoacetyl)-4-thiazolidinecarboxylic acid: amorph.; $[\alpha]_D^{25}$ −303.8° (c=0.3, MeOH).

(4R,4'R)-3,3'-[2,2'-Dithiobis(propanoyl)]bis[2-(4-fluorophenyl)-4-thiazolidinecarboxylic acid] from (4R)-2-(4-fluorophenyl)-3-(2-mercaptopropanoyl)-4-thiazolidinecarboxylic acid: mp 199°–200° C.; $[\alpha]_D^{26}$ +92.2° (c=1.0, MeOH).

(4R,4'R)-3,3'-[3,3'-Dithiobis[(2S)-2-methylpropanoyl]]bis[2-(4-dimethylaminophenyl)-4-thiazolidinecarboxylic acid] from (4R)-2-(4-dimethylaminophenyl)-3-[(2S)-3-mercapto-2-methylpropanoyl]-4-thiazolidinecarboxylic acid: amorph.; $[\alpha]_D^{25}$ +4.2° (c=0.5, MeOH).

(4R,4'R)-3,3'-[3,3'-Dithiobis[(2S)-2-methylpropanoyl]]bis[2-(4-acetaminophenyl)-4-thiazolidinecarboxylic acid] from (4R)-2-(4-acetaminophenyl)-3-[(2S)-3-mercapto-2-methylpropanoyl]-4-thiazolidinecarboxylic acid: mp 169°–173° C.; $[\alpha]_D^{25}$ +126.0° (c=1.1, MeOH).

(4R,4'R)-3,3'-[3,3'-Dithiobis(propanoyl)]bis[2-(2-carboxyphenyl)-4-thiazolidinecarboxylic acid] from (4R)-2-(2-carboxyphenyl)-3-(3-mercaptopropanoyl)-4-thiazolidinecarboxylic acid: mp 207°–208° C. (dec.); $[\alpha]_D^{25}$ +236.5° (c=0.6, MeOH).

(4R,4'R)-3,3'-[3,3'-Dithiobis(propanoyl)]bis[2-(4-hydroxyphenyl)-4-thiazolidinecarboxylic acid] from (4R)-2-(4-hydroxyphenyl)-3-(3-mercaptopropanoyl)-4-thiazolidinecarboxylic acid: amorph.; $[\alpha]_D^{26}$ +78.5° (c=1.0, MeOH).

(4R,4'R)-3,3'-[3,3'-Dithiobis(propanoyl)]bis[2-(2-hydroxy-4-methoxyphenyl)-4-thiazolidinecarboxylic acid] from (4R)-2-(2-hydroxy-4-methoxyphenyl)-3-

(3-mercaptopropanoyl)-4-thiazolidinecarboxylic acid: mp 134°–135° C. (dec.); $[\alpha]_D^{24}$ +179.0° (c=1.1, MeOH).

(4R,4'R)-3,3'-[3,3'-Dithiobis[(2S)-2-methylpropanoyl]]bis[2-(4-hydroxy-3-methoxyphenyl)-4-thiazolidinecarboxylic acid] from (4R)-2-(4-hydroxy-3-methoxyphenyl)-3-[(2S)-3-mercapto-2-methylpropanoyl]-4-thiazolidinecarboxylic acid: amorph.; $[\alpha]_D^{26}$ +104.7° (c=1.0, MeOH).

(4R,4'R)-3,3'-[3,3'-Dithiobis[(2S)-2-methylpropanoyl]]bis[2-[2-(5-methyl)furyl]-4-thiazolidinecarboxylic acid] from (4R)-3-[(2S)-3-mercapto-2-methylpropanoyl]-2-[2-(5-methyl)furyl]-4-thiazolidinecarboxylic acid: oil; $[\alpha]_D^{25}$ +78.1° (c=1.0, MeOH).

(4R,4'R)-3,3'-[3,3'-Dithiobis[(2S)-2-methylpropanoyl]]bis[2-(3-pyridyl)-4-thiazolidinecarboxylic acid] from (4R)-3-[(2S)-3-mercapto-2-methylpropanoyl]-2-(3-pyridyl)-4-thiazolidinecarboxylic acid: amorph.; $[\alpha]_D^{25}$ −13.5° (c=1.0, MeOH).

(4R,4'R)-3,3'-[3,3'-Dithiobis[(2S)-2-methylpropanoyl]]bis[2-(4-pyridyl)-4-thiazolidinecarboxylic acid] from (4R)-3-[(2S)-3-mercapto-2-methylpropanoyl]-2-(4-pyridyl)-4-thiazolidinecarboxylic acid: amorph.; $[\alpha]_D^{25}$ +64.0° (c=1.0, MeOH).

1,1'-[3,3'-Dithiobis[(2S)-2-methylpropanoyl]]bis(5-phenyl-2-pyrrolidinecarboxylic acid) from 1-[(2S)-3-mercapto-2-methylpropanoyl]-5-phenyl-2-pyrrolidinecarboxylic acid: mp 138°–142.5° C.; $[\alpha]_D^{29}$ −29.4° (c=1.0, MeOH).

1,1'-[3,3'-Dithiobis(propanoyl)]bis[5-(4-hydroxyphenyl)-2-pyrrolidinecarboxylic acid] from 1-(3-mercaptopropanoyl)-5-(4-hydroxyphenyl)-2-pyrrolidinecarboxylic acid: mp 154°–157° C.

EXAMPLE 2

(4R)-3-(3-Bromopropanoyl)-2-(2-hydroxyphenyl)-4-thiazolidinecarboxylic acid (Compound 55)

To a stirred solution of 22.5 g of (4R)-2-(2-hydroxyphenyl)-4-thiazolidinecarboxylic acid and 21.2 g of sodium carbonate in 200 ml of water, cooled by an ice-water bath, 18.8 g of 3-bromopropanoyl chloride is added dropwise. The resulting mixture is continuously stirred for 2 hr at room temperature, acidified with 2 N aqueous hydrochloric acid solution, and extracted with 300 ml of ethyl acetate. The organic layer is washed with brine and dried over sodium sulfate. After removal of ethyl acetate in vacuo, 100 ml of chloroform is added to the residue and the separated crystals are filtered to give 24.3 g (70%) of the product. The product is recrystallized from methanol to yield the titled compound: mp 109°–115° C.; IR (nujol) 3330, 1709, 1629, 1594, 1229, 1198, 1029 cm$^{-1}$.

EXAMPLE 3

(4R,4'R)-3,3'-[3,3'-Dithiobis(propanoyl)]bis[2-(2-hydroxyphenyl)-4-thiazolidinecarboxylic acid] (Compound 1)

A solution of 6.9 g of compound 55 in 15 ml of ethanol is mixed with a solution of 5 g of sodium thiosulfate in 7.5 ml of water. The resulting mixture is refluxed for 5 hr and evaporated in vacuo. After addition of 50 ml of ether, the crude product is collected to give 9.2 g of the Bunte's salt. A solution of 9.2 g of the Bunte's salt in 40 ml of 2 N aqueous potassium hydroxide solution is heated for 1 hr and acidified with 2 N aqueous hydrochloric acid solution. The precipitated crystals of the titled compound are filtered. The yield is 2.8 g (45%).

These crystals are identical with those described in Example 1. The compounds shown in Table I are prepared by the same method as described above.

EXAMPLE 4

(4R,4'R)-3,3'-[3,3'-Dithiobis(propanoyl)]bis[2-(2-hydroxyphenyl)-4-thiazolidinecarboxylic cid] (Compound 1)

To a stirred solution of 4.7 g of (4R)-2-(2-hydroxyphenyl)-3-(3-mercaptopropanoyl)-4-thiazolidinecarboxylic acid in 150 ml of ethyl acetate, a solution of 5 ml of carbon tetrachloride containing 0.7 g of dinitrogen tetraoxide is added dropwise at −20° C. in dark. The resulting mixture is warmed until 0° C. is reached with stirring, maintained the same temperature for 2 hr, and then 50 ml of ice-water is added. The organic layer is washed with brine, dried over sodium sulfate, and concentrated in vacuo. The separated crystals of the titled compound are filtered. The yield is 2.9 g (62%).

Those crystals are identical with those described in Example 1. The compounds shown in Table I and II are prepared by the same method as described above.

EXAMPLE 5

(4R,4'R)-3,3'-[3,3'-Dithiobis[(2S)-2-methylpropanoyl]]bis[2-(2-hydroxyphenyl)-4-thiazolidinecarboxylic acid] (Compound 2)

To a stirred solution of 2.3 g of (4R)-2-(2-hydroxyphenyl)-4-thiazolidinecarboxylic acid and 2.1 g of sodium carbonate in 20 ml of water, cooled by an ice-water bath, is added dropwise 1.6 g (2S,2'S)-3,3'-dithiobis(2-methylpropanoyl chloride), prepared from thionyl chloride and (2S,2'S)-3,3'-dithiobis(2-methylpriopanoic acid): mp 125°–126.5° C.; $[\alpha]_D^{24}$ −220° (c=0.5, 0.5 N aqueous ammonia solution). The resulting mixture is continuously stirred for 1 hr, then acidified with 2 N aqueous hydrochloric acid solution. The separated crystals of the titled compound are filtered. The yield is 3.0 g (90%).

The compounds shown in Table I are prepared by the same method as described above. Similarly the compounds shown below are prepared according to this method.

(4R,4'R)-3,3'-[3,3'-Dithiobis(propanoyl)]bis[2-(S-acetyl-2-mercaptoethyl)-4-thiazolidinecarboxylic acid] from (4R)-2-(S-acetyl-2-mercaptoethyl)-4-thiazolidinecarboxylic acid: mp 159° C. (dec.).

(4R,4'R)-3,3'-Dithiobis(propanoyl)]bis[2-(4-benzyloxycarbonylaminophenyl)-4-thiazolidinecarboxylic acid] from (4R)-2-(4-benzoyloxycarbonylaminophenyl)-4-thiazolidinecarboxylic acid: mp 147°–150° C. (dec.).

(4R,4'R)-3,3'-[3,3'-Dithiobis[(2S)-2-methylpropanoyl]]bis[2-(3-benzoyloxyphenyl)-4-thiazolidinecarboxylic acid] from (4R)-2-(3-benzoyloxyphenyl)-4-thiazolidinecarboxylic acid: mp 156° C. (dec.); $[\alpha]_D^{26}$ −105° (c=1.0, DMSO).

(4R,4'R)-3,3'-[3,3'-Dithiobis[(2S)-2-methylpropanoyl]]bis[2-(4-benzyloxycarbonyloxyphenyl)-4-thiazolidinecarboxylic acid] from (4R)-2-(4-benzyloxycarbonyloxyphenyl)-4-thiazolidinecarboxylic acid: mp 153° C. (dec.); $[\alpha]_D^{26}$ −87.5° (c=1.0, DMSO).

(4R,4'R)-3,3'-[3,3'-Dithiobis(propanoyl)]bis[2-(3,4-dihydroxyphenyl)-4-thiazolidinecarboxylic acid] from (4R)-2-(3,4-dihydroxyphenyl)-4-thiazolidinecarboxylic acid: mp 174°–175° C. (dec.); $[\alpha]_D^{23}$ −105.2° (c=0.6, DMSO).

(4R,4′R)-3,3′-[3,3′-Dithiobis(propanoyl)]bis[2-(3-methoxy-4-pivaloyloxyphenyl)-4-thiazolidinecarboxylic acid] from (4R)-2-(3-methoxy-4-pivaloyloxyphenyl)-4-thiazolidinecarboxylic acid: mp 129°–130° C. (dec.); $[\alpha]_D^{26}$ −86.7° (c=1.0, DMSO).

EXAMPLE 6

(4R,4′R)-3,3′-[3,3′-Dithiobis[(2S)-2-methylpropanoyl]]bis[2-(4-methoxyphenyl)-4-thiazolidinecarboxylic acid] (Compound 12)

To a stirred solution of 1.2 g of (2S,2′S)-3,3′-dithiobis(2-methylpropanoic acid) and 1.4 ml of triethylamine in 15 ml of anhydrous tetrahydrofuran, cooled at −10° C., 1.3 ml of isobutyl chloroformate is added dropwise. The resulting slurry is continuously stirred for 10 min at this temperature, then a solution of 2.4 g of (4R)-2-(4-methoxyphenyl)-4-thiazolidinecarboxylic acid and 1.4 ml of triethylamine in 3 ml of water and 10 ml of tetrahydrofuran is added. The resulting mixture is stirred for 1 hr and acidified with 0.5 N aqueous hydrochloric acid solution. The separated crystals of the titled compound are filtered. The yield is 1.6 g (47%).

The compounds shown in Table I and II are prepared by the same method as described above.

EXAMPLE 7

Sodium (4R,4′R)-3,3′-[3,3′-dithiobis(propanoyl)]bis[2-(2-hydroxyphenyl)-4-thiazolidinecarboxylate] (Compound 5)

To a stirred solution of 22.5 g of (4R)-2-(2-hydroxyphenyl)-4-thiazolidinecarboxylic acid and 14.9 g of sodium carbonate in 300 ml of water, cooled by an ice-water bath, 14.6 g of 3,3′-dithiodipropanoyl dichloride is added dropwise. The resulting mixture is continuously stirred for 1 hr, acidified with concentrated hydrochloric acid, and extracted with ethyl acetate. The organic layer is washed with brine, dried over magnesium sulfate, and evaporated in vacuo. The residue is dissolved in N aqueous sodium hydroxide solution and the resulting solution is acidified with N aqueous hydrochloric acid solution. The separated crystals are filtered and dissolved in N aqueous sodium hydroxide solution. To the resulting solution is added isopropyl alcohol and then the separated crystals of the titled compound are filted. The yield is 26.9 g (80%).

This sodium salt is dissolved in water and then the resulting solution is acidified with N aqueous hydrochloric acid solution to give the free acid of the titled compound which is identical with compound 1 described in Example 1. The salt can also be prepared from sodium hydroxide and compound 1 obtained by another procedure.

The potassium salt (compound 6) is prepared by the use of potassium hydroxide instead of sodium hydroxide.

EXAMPLE 8

(4R,4′R)-3,3′-[3,3′-Dithiobis(propanoyl)]bis[2-(2-hydroxyphenyl)-4-thiazolidinecarboxylic acid] (Compound 1)

To 1.6 g of sodium sulfide dissolved in 30 ml of 95% ethanol, 0.7 g of sulfur is added while refluxing. The resulting mixture is stirred until the sulfur dissolves. This hot solution is added to a solution of 7.4 g of the compound 55 obtained in Example 2 and 0.9 g of sodium hydroxide in 30 ml of 95% ethanol under gentle reflux. The resulting solution is refluxed for 3 hr, allowed to stand overnight, and concentrated in vacuo. After addition of 50 ml of water, the remaining solution is acidified with 2 N aqueous hydrochloric acid solution. The separated crystals of the titled compound are filtered. The yield is 3.9 g (58%).

These crystals is identical with those described in Example 1. The compounds shown in Table I are prepared by the same method as described above.

EXAMPLE 9

(4R)-2-(2-Hydroxyphenyl)-3-(3-propyldisulfanylpropanoyl)-4-thiazolidinecarboxylic acid (Compound 34)

To a stirred solution of 3.1 g of (4R)-2-(2-hydroxyphenyl)-3-(3-mercaptopropanoyl)-4-thiazolidinecarboxylic acid in 30 ml of N aqueous sodium hydroxide solution, is added 3.6 g of sodium propylthiosulfate, obtained by evaporation of a refluxed solution of propyl bromide and sodium thiosulfate in ethanol-water solution for 2 hr, then filtration after addition of ethanol to the residue and evaporation of the filtrate. The resulting solution is continuously stirred for 1 min at room temperature, acidified with 10% aqueous hydrochloric acid solution, and extracted with ethyl acetate. The organic layer is washed with brine, dried over sodium sulfate, and evaporated in vacuo. The residual oil is purified by column chromatography on silica gel to give the titled compound as an amorphous powder. The yield is 1.2 g (31%).

The compounds shown in Table IV and V are prepared by the same procedure as described above. Similarly the compounds shown below are prepared according to this method.

(4R)-3-[3-(2-Hydroxyethyldisulfanyl)propanoyl]-2-(2-hydroxyphenyl)-4-thiazolidinecarboxylic acid from (4R)-2-(2-hydroxyphenyl)-3-(3-mercaptopropanoyl)-4-thiazolidinecarboxylic acid.

(4R)-3-(3-Benzyldisulfanylpropanoyl)-2-(2-hydroxyphenyl)-4-thiazolidinecarboxylic acid from (4R)-2-(2-hydroxyphenyl)-3-(3-mercaptopropanoyl)-4-thiazolidinecarboxylic acid.

1-(3-Allyldisulfanylpropanoyl)-5-(2-hydroxyphenyl)-2-(pyrrolidinecarboxylic acid from 5-(2-hydroxyphenyl)-1-(3-mercaptopropanoyl)-2-pyrrolidinecarboxylic acid.

5-(2-Hydroxyphenyl)-1-[3-[(tetrahydrofurfuryl)disulfanyl]propanoyl]-2-pyrrolidinecarboxylic acid from 5-(2-hydroxyphenyl)-1-(3-mercaptopropanoyl)-2-pyrrolidinecarboxylic acid.

(4R)-3-[(2S)-3-Allyldisulfanyl-2-methylpropanoyl]-4-thiazolidinecarboxylic acid from (4R)-3-[(2S)-3-mercapto-2-methylpropanoyl]-4-thiazolidinecarboxylic acid.

Ethyl (4R)-3-[(2S)-2-methyl-3-propyldisulfanylpropanoyl]-4-thiazolidinecarboxylate from ethyl (4R)-3-[(2S)-3-mercapto-2-methylpropanoyl]-4-thiazolidinecarboxylate.

(4R)-3-[(2S)-2-Methyl-3-octyldisulfanylpropanoyl]-4-thiazolidinecarboxylic acid from (4R)-3-[(2S)-3-mercapto-2-methylpropanoyl]-4-thiazolidinecarboxylic acid.

(2S)-1-[(2S)-3-Allyldisulfanyl-2-methylpropanoyl]proline from (2S)-1-[(2S)-3-mercapto-2-methylpropanoyl]proline.

(2S)-1-[(2S)-2-Methyl-3-octyldisulfanylpropanoyl]proline ethyl ester from (2S)-1-[(2S)-3-mercapto-2-methylpropanoyl]-proline ethyl ester.

EXAMPLE 10

(4R)-3-(3-Ethyldisulfanylpropanoyl)-2-(2-hydroxyphenyl)-4-thiazolidinecarboxylic acid (Compound 31)

To a stirred solution of 2.3 g of methyl ethyldisulfanylformate in 10 ml of methanol, obtained by the reaction of ethylmercaptan with carbomethoxysulfenyl chloride at ca. 0° C. for 1 hr in methanol solution and then distillation of the resulting mixture, a solution of 4.7 g of (4R)-2-(2-hydroxyphenyl)-3-(3-mercaptopropanoyl)-4-thiazolidinecarboxylic acid and 2.1 ml of triethylamine in 20 ml of methanol is added dropwise at room temperature. After addition, the resulting solution is instantly acidified with 2 N aqueous hydrochloric acid solution and 150 ml of ethyl acetate and 50 ml of water are added. The organic layer is washed with brine, dried over sodium sulfate, and evaporated in vacuo. The residual oil is purified by column chromatography on silica gel to give the titled compound as oil. The yield is 1.2 g (31%).

The compounds shown in Table IV and V are prepared by the same method as described above.

EXAMPLE 11

(4R)-2-(2-Hydroxyphenyl)-3-(3-octyldisulfanylpropanoyl)-4-thiazolidinecarboxylic acid (Compound 36)

A solution of 2.3 g of (4R)-2-(2-hydroxyphenyl)-3-(3-mercaptopropanoyl)-4-thiazolidinecarboxylic acid and 2.9 g of N-(octylthio)phthalimide in 50 ml of ethanol, obtained by the addition of bromine to dioctyl disulfide or octylmercaptan in carbon tetrachloride at 0° C. then treatment with phthalimide and triethylamine in carbon tetrachloride at room temperature for 2 hr and removal of the carbon tetrachloride after washing with water, is refluxed for 1 hr. After cooling, phthalimide is filtered off, then the filtrate is evaporated in vacuo and the residual oil is purified by column chromatography on silica gel to give the titled compound as oil. The yield is 1.2 g (26%).

The compounds shown in Table IV and V are prepared by the same method as described above.

EXAMPLE 12

(4R)-3-[(2S)-3-[[(4R)-2-(2-Hydroxyphenyl)-4-carboxythiazolidin-3-yl]carbonylethyldithio]-2-methylpropanoyl]-4-thiazolidinecarboxylic acid (Compound 40)

To a stirred solution of 2.4 g of (4R)-3-[(2S)-3-mercapto-2-methylpropanoyl]-4-thiazolidinecarboxylic acid in 60 ml of N aqueous sodium hydroxide solution, 9.2 g of the Bunte's salt described in Example 3 is added. The resulting solution is continuously stirred for 1 min at room temperature, acidified with 10% aqueous hydrochloric acid solution, and extracted with ethyl acetate. The organic layer is washed with brine, then dried over sodium sulfate, and evaporated in vacuo. The residual oil is purified by column chromatography on silica gel to give the titled compound as an amorphous powder. The yield is 0.8 g (14%).

EXAMPLE 13

(4R)-3-[(2S)-3-[[(4R)-2-(2-Hydroxyphenyl)-4-carboxythiazolidin-3-yl]carbonylethyldithio]-2-methylpropanoyl]-4-thiazolidinecarboxylic acid (Compound 40)

To a stirred solution of 1.9 g of compound 1 in 6 ml of N aqueous sodium hydroxide solution, is added a solution of 0.7 g of (4R)-3-[(2S)-3-mercapto-2-methylpropanoyl]-4-thiazolidinecarboxylic acid in 3 ml of N aqueous sodium hydroxide solution. The resulting mixture is continuously stirred for 30 min, acidified with N aqueous hydrochloric acid solution, and extracted with 30 ml of ethyl acetate. The organic layer is washed with brine, dried over sodium sulfate, and evaporated in vacuo. The residual oil is purified by column chromatography on silica gel to give the titled compound as an amorphous powder. The yield is 0.2 g (12%).

This powder is identical with that described in Example 12.

The compounds shown below are also prepared according to the same procedure as described above.

(4R)-3-[3-[[(2R)-2-Amino-2-carboxyethyl]dithio]propanoyl]-2-(2-hydroxyphenyl)-4-thiazolidinecarboxylic acid from (4R)-2-(2-hydroxyphenyl)-3-(3-mercaptopropanoyl)-4-thiazolidinecarboxylic acid and L-cystine, (4R)-3-[3-[1-(Carboxymethylcarbamoyl)ethyldithio]propanoyl]-2-(2-hydroxyphenyl)-4-thiazolidinecarboxylic acid from (4R4'R)-3,3'-[3,3'-dithiobis(propanoyl)]bis[2-(2-hydroxyphenyl)-4-thiazolidinecarboxylic acid] and tiopronin.

(4R)-3-[3-[1-Methyl-1-[(1R)-S-pivaloyl-1-carboxy-2-mercaptoethylcarbamoyl]ethyldithio]propanoyl]-2-(2-hydroxyphenyl)-4-thiazolidinecarboxylic acid from (4R,4'R)-3,3'-[3,3'-dithiobis(propanoyl)]bis[2-(2-hydroxyphenyl)-4-thiazolidinecarboxylic acid] and N-(2-mercapto-2-methylpropanoyl)-S-pivaloyl-L-cysteine: mp 115°–117° C. $[\alpha]_D^{27}$ −25.7° (c=1.1, MeOH).

EXAMPLE 14

(4R)-3-[3-(2-Carboxyethyldisulfanyl)propanoyl]-2-(2-hydroxyphenyl)-4-thiazolidinecarboxylic acid (Compound 41)

To a stirred solution of 2.0 g of (4R)-2-hydroxyphenyl-4-thiazolidinecarboxylic acid and 1.7 ml of triethylamine in 15 ml of anhydrous acetone, 2.0 g of dithiodipropanoic anhydride is added. The resulting mixture is continuously stirred for 40 min at room temperature and extracted with ethyl acetate after addition of 50 ml of water containing a small amount of potassium carbonate. The aqueous layer is acidified with N aqueous hydrochloric acid and extracted with ethyl acetate. The second organic layer is washed with brine, dried over magnesium sulfate, and evaporated in vacuo. The residual oil is purified by column chromatography on silica gel to give crystals of the titled compound. The yield is 0.6 g (15%).

EXAMPLE 15

Diethyl (4R,4'R)-3,3'-[3,3'-dithiobis(propanoyl)]bis[2-(2-hydroxyphenyl)-4-thiazolidinecarboxylate] (Compound 51)

To 2.35 g of ethyl (4R)-2-(2-hydroxyphenyl)-4-thiazolidinecarboxylate: mp 75°–77° C.; $[\alpha]_D^{25}$ −105.1° (c=0.9, methanol), obtained by the reaction of L-cysteine ethyl ester hydrochloride with salicylaldehyde in the presence of triethylamine in chloroform at room temperature for 2 hr then addition of water and evaporation of the organic layer, which is dissolved in 30 ml of water and 40 ml of tetrahydrofuran, 1.1 g of sodium carbonate is added. To the stirred mixture, cooled by an ice-water bath, 1.36 g of 3,3'-dithiodipropanoyl dichloride is added dropwise. The resulting mixture is continuously stirred for 30 min and extracted with ether after addition of 100 ml of water. The organic layer is washed with brine, dried over magnesium sulfate, and evaporated in vacuo to give crystals of the titled compound. The yield is 2.3 g (68%).

The compounds shown in Table IV are prepared by the same method as described above.

EXAMPLE 16

Bis[(2,2-dimethyl-1-oxopropoxy)methyl] (4R,4'R)-3,3'-[3,3'-dithiobis(propanoyl)]bis[2-(2-hydroxyphenyl)-4-thiazolidinecarboxylate] (Compound 49)

To a stirred solution of 3.12 g of compound 1 obtained in Example 1 in 15 ml of anhydrous N,N-dimethylformamide, 1.4 ml of triethylamine and 1.5 g of chloromethyl pivalate are added. The resulting mixture is continuously stirred at room temperature overnight, then poured into 30 ml of ice-water, and extracted with ether. The organic layer is washed with brine, dried over magnesium sulfate, and evaporated in vacuo. The residual oil is purified by column chromatography on silica gel to give crystals of the titled compound. The yield is 2.1 g (49%).

The compounds shown in Table VI and VII are prepared by the same procedure as described above. Similarly the compounds shown below are prepared according to this method.

(2,2-Dimethyl-1-oxopropoxy)methyl (4R)-2-(2-hydroxyphenyl)-3-(3-propyldisulfanylpropanoyl)-4-thiazolidinecarboxylate from (4R)-2-(2-hydroxyphenyl)-3-(3-propyldisulfanylpropanoyl)-4-thiazolidinecarboxylic acid.

(2,2-Dimethyl-1-oxopropoxy)methyl (4R)-3-(3-allyldisulfanylpropanoyl)-2-(2-hydroxyphenyl)-4-thiazolidinecarboxylate from (4R)-3-(3-allyldisulfanylpropanoyl)-2-(2-hydroxyphenyl)4-thiazolidinecarboxylic acid.

Bis[(2,2-dimethyl-1-oxopropoxy)methyl] 1,1'-[3,3'-dithiobis (propanoyl)]bis[5-(2-hydroxyphenyl)-2-pyrrolidinecarboxylate] from 1,1'-[3,3'-dithiobis(-propanoyl)]bis[5-(2-hydroxyphenyl)-2-pyrrolidinecarboxylic acid].

(2,2-Dimethyl-1-oxopropoxy)methyl 5-(2-hydroxyphenyl)-1-[(2S)-2-methyl-3-propyldisulfanylpropanoyl]-2-pyrrolidinecarboxylate from 5-(2-hydroxyphenyl)-1-[(2S)-2-methyl-3-propyldisulfanylpropanoyl]-2-pyrrolidinecarboxylic acid.

(2,2-Dimethyl-1-oxopropoxy)methyl (4R)-3-[(2S)-2-methyl-3-propyldisulfanylpropanoyl]-4-thiazolidinecarboxylate from (4R)-3-[(2S)-2-methyl-3-propyldisulfanylpropanoyl]-4-thiazolidinecarboxylic acid.

(2,2-Dimethyl-1-oxopropoxy)methyl (4R)-3-[(2S)-2-methyl-3-[(tetrahydrofurfuryl)disulfar 1]propanoyl]-4-thiazolidinecarboxylate from (4R)-3-[(2S)-2-methyl-3-[(tetrahydrofurfuryl)disulfanyl]propanoyl]-4-thiazolidinecarboxylic acid.

(2S)-1-[(2S)-2-Methyl-3propyldisulfanylpropanoyl]proline (2,2-dimethyl-1-oxopropoxy)methyl ester from (2S)-1-[(2S)-2-methyl-3-propyldisulfanylpropanoyl]-proline: mp 79°–81° C.; $[\alpha]_D^{25}$ −185.2° (c=0.5, MeOH).

(2S)-1-[(2S)-2-Methyl-3-[(tetrahydrofurfuryl)disulfanyl]propanoyl]proline (2,2-dimethyl-1-oxopropoxy)methyl ester from (2S)-1-[(2S)-2-methyl-3-[(tetrahydrofurfuryl)disulfanyl]propanoyl]proline.

Bis[(2,2-dimethyl-1-oxopropoxy)methyl] (4R,4'R)-3,3'-[3,3'-dithiobis(propanoyl)]bis[2-(4-methoxyphenyl)-4-thiazolidinecarboxylate] from (4R,4'R)-3,3'-[3,3'-dithiobis(propanoyl)]bis[2-(4-methoxyphenyl)-4-thiazolidinecarboxylic acid].

Bis [(2,2-dimethyl-1-oxopropoxy)methyl] (4R,4'R)-3,3'-[3,3'-dithiobis[(2S)-2-methylpropanoyl]]bis[2-(3-nitophenyl)-4-thiazolidinecarboxylate] from (4R,4'R)-3,3'-[3,3'-dithiobis[(2S)-2-methylpropanoyl]]bis[2-(3-nitrophenyl)-4-thiazolidinecarboxylic acid].

Bis[(2,2-dimethyl-1-oxopropoxy)methyl] (4R,4'R)-3,3'-[3,3'-dithiobis[(2S)-2-methylpropanoyl]]bis[2-(5-chloro-2-hydroxyphenyl)-4-thiazolidinecarboxylate] from (4R,4'R)-3,3'-[3,3'-dithiobis[(2S)-2-methylpropanoyl]]bis[2-(5-chloro-2-hydroxyphenyl)-4-athiazolidinecarboxylic acid].

Bis[(2,2-dimethyl-1-oxopropoxy)methyl] (4R,4'R)-3,3'-[3,3'-dithiobis[(2S)-2-methylpropanoyl]]bis[2-(4-methylphenyl)-4-thiazolidinecarboxylate] from (4R,4'R)-3,3'-[3,3'-dithiobis[(2S)-2-methylpropaneyl]-[bis[2-(4-methylphenyl)-4-thiazolidinecarboxylic acid].

Bis[(2,2-dimethyl-1-oxopropoxy)methyl] (4R,4'R)-3,3'-[3,3'-dithiobis(propanoyl)]bis[2-(2-hydroxy-3-methoxyphenyl)-4-thiazolidinecarboxylate) from (4R,4'R)-3,3'-[3,3'-dithiobis propanoyl)]bis[2-(2-hydroxy-3-methoxyphenyl)-4-thiazolidinecarboxylic acid].

Bis[1-(2,2-dimethyl-1-oxopropoxy)ethyl] (4R,4'R)-3,3'-[3,3'-dithiobis[(2S)-2-methylpropanoyl]]bis[2-(3,4,5-trimethoxyphenyl)-4-thiazolidinecarboxylate] from (4R,4'R)-3,3'-[3,3'-dithiobis[(2S)-2-methylpropanoyl]]bis[2-(3,4,5-trimethoxyphenyl)-4-thiazolidinecarboxylic acid].

Bis [(2,2-dimethyl-1-oxopropoxy)methyl] (4R,4'R)-3,3'-[3,3'-dithiobis(propanoyl)]bis[2-(S-acetyl-2-mercaptoethyl)-4-thiazolidinecarboxylate] from (4R,4'R)-3,3'-[3,3'-dithiobis (propanoyl]bis[2-(S-acetyl-2-mercaptoethyl)-4-thiazolidinecarboxylic acid].

EXAMPLE 17

Bis [2-(1,3-dihydro-1,3-dioxo-2H-isoindol-2-yl)ethyl] (4R,4'R) 3,3'-[3,3'-dithiobis(propanoyl)]bis[2-(2-hydroxyphenyl)-4-thiazolidinecaboxylate] (Compound 48)

To a stirred solution of 3.12 g of compound 1 obtained in Example 1 in 15 ml of anhydrous N,N-dimethylformamide, 1.4 ml of triethylamine and 2.54 g of N-(2-bromoethyl)phthalimide are added. The resulting mixture is continuously stirred for 6 hr at 90° C. under a nitrogen atmosphere, poured into 30 ml of ice-water, and extracted with ether. The organic layer is washed with brine, dried over magnesium sulfate, and evaporated in vacuo. The residual oil is purified by column chromatography on silica gel to give the titled compound as an amorphous. The yield is 2.1 g (43%).

The compounds shown in Table VI are prepared by the same procedure as described above. Similarly the compounds shown below are prepared according to this method.

Bis [(1,3-dihydro-1,3-dioxo-2H-isoindol-2-yl)methyl] (4R,4'R)-3,3'-[3,3'-dithiobis[(2S)-2-methylpropanoyl]]bis(4-thiazolidinecarboxylate) from (4R,4'R)-3,3'-[3,3'-dithiobis[(2S)-2-methylpropanoyl]]bis(4-thiazolidinecarboxylic acid).

Bis[2-(1,3-dihydro-1,3-dioxo-2H-isoindol-2-yl)ethyl] (2S,2'S)-1,1'-[3,3'-dithiobis[(2S)-2-methylpropanoyl]-

]bis(proline) from (2S,2'S)-1,1'-[3,3'-Dithiobis[(2S)-2methylpropanoyl]] bis(proline).

Bis[(1,3-dihydro-1,3-dioxo-2H-isoindol-2-yl)methyl] (4R,4'R)-3,3'-[3,3'-dithiobis[(2S)-2-methyl-propanoyl]]bis[2-(2-furyl)-4-thiazolidinecarboxylate] from (4R,4'R)-3,3'-[3,3'-dithiobis [(2S)-2-methyl-propanoyl]]bis[2-(2-furyl)-4-thiazolidinecarboxylic acid].

Bis[2-(1,3-dihydro-1,3-dioxo-2H-isoindol-2-yl)ethyl] (4R,4'R)-3,3'-[3,3'-dithiobis(propanoyl)]bis[2-(2-thienyl)-4-thiazolidinecarboxylate] from (4R,4'R)-3,3'-[3,3'-dithiobis (propanoyl)]bis[2-(2-thienyl)-4-thiazolidiecarboxylic acid].

Bis[(2,5-dioxo-1-pyrrolidinyl)methyl] (4R,4'R)-3,3'-[3,3'-dithiobis(propanoyl)]bis[2-(2-hydroxyphenyl)-4-thiazolidinecarboxylate] from (4R,4'R)-3,3'-[3,3'-dithiobis(propanoyl)] bis[2-(2-hydroxyphenyl)-4-thiazolidinecarboxylic acid].

Bis[1-(2,5-dioxo-1-pyrrolidinyl)ethyl] (4R,4'R)-3,3'-[3,3'-dithiobis(propanoyl)]bis[2-(2-hydroxyphenyl)-4-thiazolidinecarboxylate] from (4R,4'R)-3,3'-[3,3'-dithiobis(propanoyl)] bis[2-(2-hydroxyphenyl)-4-thiazolidinecarboxylic acid].

EXAMPLE 18

(4R,4'R)-3,3'-[3,3'-Dithiobis(propanoyl)]bis[2-(2-acetoxyphenyl)-4-thiazolidinecarboxylic acid] (Compound 3)

To a stirred solution of 1.3 g of compound 1 obtained in Example 1 in 8.6 ml of N aqueous sodium hydroxide solution, 0.42 ml of acetic anhydride is added dropwise at room temperature, and acidified with concentrated hydrochloric acid. The separated crystals of the titled compound are filtered. The yield is 1.3 g (92%).

The compounds shown below are also prepared according to the same procedure as described above.

(4R,4'R)-3,3'-[3,3'-Dithiobis(propanoyl)]bis[2-(2-propanoyloxyphenyl)-4-thiazolidinecarboxylic acid] from (4R,4'R)-3,3'-[3,3'-dithiobis(propanoyl)]bis[2-(2-hydroxyphenyl)-4-thiazolidinecarboxylic acid].

1,1'-[3,3'-Dithiobis(propanoyl)]bis[5-(2-acetoxyphenyl)-2-pyrrolidinecarboxylic acid] from 1,1'-[3,3'-dithiobis (propanoyl)]bis[5-(2-acetoxyphenyl)-2-pyrrolidinecarboxylic acid].

TABLE I

Symmetrical Disulfides

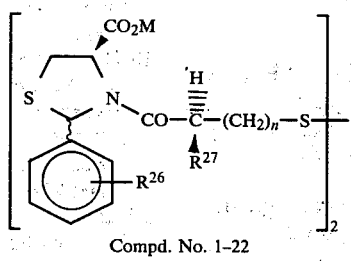

Compd. No. 1–22

| Compd. No. | R²⁶ | R²⁷ | n | M | Method of prepn. (Examp. No.) | Yield (%) | mp (°C.) | Recrystn. solvent | [α]$_D$ deg. (c. solv., °C.) | IR (nujol, cm⁻¹) | Rf value (SiO₂) (corresponding thiol) |
|---|---|---|---|---|---|---|---|---|---|---|---|
| 1 | 2-OH | H | 1 | H | 1 | 93 | 187 (dec.) | AcOEt | +165.1 (1.1, MeOH, 25) | 3360, 1722, 1622, 1600, 1452, 1232, 763 | 0.26*¹ (0.45) |
|   |     |   |   |   | 3 | 45 |            |        |                        |                                         |               |
|   |     |   |   |   | 4 | 62 |            |        |                        |                                         |               |
|   |     |   |   |   | 5 | 85 |            |        |                        |                                         |               |
|   |     |   |   |   | 6 | 52 |            |        |                        |                                         |               |
|   |     |   |   |   | 8 | 58 |            |        |                        |                                         |               |
| 2 | 2-OH | CH₃ | 1 | H | 1 | 91 | 154–157 (dec.) | MeOH—H₂O | +76.9 (1.0, MeOH, 23) | 3200, 1723, 1634, 1601, 1304, 1236, 1212 | 0.34*¹ (0.49) |
|   |     |   |   |   | 3 | 38 |            |        |                        |                                         |               |
|   |     |   |   |   | 5 | 90 |            |        |                        |                                         |               |
| 3 | 2-OCOCH₃ | H | 1 | H | 5 | 35 | 119–120 (dec.) (amorph.) |  | +116.9 (1.0, MeOH, 24) | 1765, 1738, 1645, 1453, 1410, 1200, 1173, 1096, 762 |  |
|   |     |   |   |   | 18 | 92 |           |        |                        |                                         |               |
| 4 | 2-OH | H | 2 | H | 1 | 70 | 110–124 (amorph.) | MeOH—H₂O | +141.4 (1.0, MeOH 26) | 3180, 1723, 1610, 1282, 1231, 1173, 1094 | 0.33*³ (0.58) |
|   |     |   |   |   | 6 | 31 |           |        |                        |                                         |               |
| 5 | 2-OH | H | 1 | Na | 7 | 80 | 195 (dec.) | H₂O—i-PrOH | +175.1 (0.9, MeOH, 25) | 3320$^{br}$, 1595, 1446, 1381, |  |
| 6 | 2-OH | H | 1 | K | 7 | 79 | 180 (dec.) | H₂O—i-PrOH | +164.9 (1.1, MeOH, 25) | 3320$^{br}$, 1595, 1446, 1381 |  |
| 7 | H | H | 1 | H | 1 | 61 | 97–102 | EtOH—H₂O | +109.0 (0.5, MeOH, 26) | 1730, 1640, 1610, 730 | 0.20*² (0.41) |
|   |   |   |   |   | 5 | 53 |        |          |                        |                      |               |
|   |   |   |   |   | 8 | 56 |        |          |                        |                      |               |
| 8 | 4-CH₃ | CH₃ | 1 | H | 1 | 97 | 99–105 (amorph.) |  | +114.2 (0.5, MeOH, 23) | 1725, 1620, 1600, 820 | 0.51*¹ (0.65) |
|   |      |     |   |   | 4 | 71 |        |          |                        |                      |               |
|   |      |     |   |   | 3 | 51 |        |          |                        |                      |               |
| 9 | 3-NO₂ | CH₃ | 1 | H | 1 | 93 | 120–125 |  | +38.2 | 1738, 1635, | 0.24*¹ |

TABLE I-continued
Symmetrical Disulfides

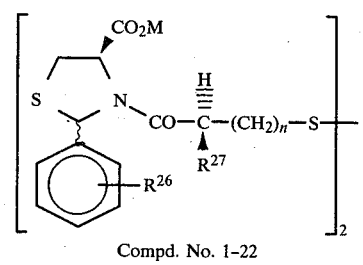

Compd. No. 1-22

| Compd. No. | $R^{26}$ | $R^{27}$ | n | M | Method of prepn. (Examp. No.) | Yield (%) | mp (°C.) | Recrystn. solvent | $[\alpha]_D$ deg. (c. solv., °C.) | IR (nujol, cm$^{-1}$) | Rf value (SiO$_2$) (corresponding thiol) |
|---|---|---|---|---|---|---|---|---|---|---|---|
|  |  |  |  |  | 5 | 76 | (dec.) (amorph.) |  | (0.5, MeOH, 25) | 1523, 730 | (0.50) |
| 10 | 3-OH | H | 1 | H | 1 | 87 | 88–116 |  | +113.6 | 3320, 1720, | 0.32*[1] |
|  |  |  |  |  | 5 | 80 | (amorph.) |  | (0.5, MeOH, 23) | 1625, 780, 750 | (0.60) |
|  |  |  |  |  | 8 | 59 |  |  |  |  |  |
| 11 | 2-OH, 5-Cl | CH$_3$ | 1 | H | 1 | 100 | 147–155 |  | +24.3 | 3320, 1735, | 0.51*[1] |
|  |  |  |  |  | 5 | 91 | (amorph.) |  | (0.5, MeOH, 23) | 1650, 1610, 780 | (0.67) |
| 12 | 4-OCH$_3$ | CH$_3$ | 1 | H | 1 | 94 | 102–121 |  | +32.6 | 1737, 1610, | 0.24*[1] |
|  |  |  |  |  | 6 | 47 | (amorph.) |  | (0.5, MeOH, 25) | 1243, 842, 785 | (0.56) |
| 13 | 2-OH, 3-OCH$_3$ | H | 1 | H | 1 | 76 | 117–131 |  | +128.3 | 3400, 1720, | 0.23*[1] |
|  |  |  |  |  | 3 | 29 | (amorph.) |  | (0.5, MeOH, 23) | 1635, 1605, 770, 745 | (0.74) |
|  |  |  |  |  | 5 | 59 |  |  |  |  |  |
| 14 | 3,4-OCH$_2$O— | CH$_3$ | 1 | H | 1 | 87 | 116–125 |  | +37.3 | 1740, 1619, | 0.29*[1] |
|  |  |  |  |  | 4 | 65 | (amorph.) |  | (0.5, MeOH, 25) | 1240, 1039, 930 | (0.73) |
| 15 | 2-OH | H | 0 | H | 1 | 97 | 128–129 (dec.) | MeOH—H$_2$O | +231.4 | 3420, 1723, | 0.12*[3] |
|  |  |  |  |  | 6 | 47 |  |  | (0.5, MeOH, 26) | 1629, 1284, 1239, 1202, 1097 | (0.39) |
| 16 | 4-OCH$_3$ | H | 1 | H | 1 | 100 | 85–104 |  | +127.5 | 1740, 1635, | 0.33*[1] |
|  |  |  |  |  | 5 | 82 | (amorph.) |  | (1.0, MeOH, 26) | 1610, 1177, 1030, 846 | (0.55) |
| 17 | 3,4,5-(OCH$_3$)$_3$ | CH$_3$ | 1 | H | 1 | 90 | 115–122 |  | +76.5 | 1738, 1640, | 0.24*[1] |
|  |  |  |  |  | 4 | 71 | (amorph.) |  | (1.1, MeOH, 26) | 1592, 1230, 1180, 1125, 1005 | (0.42) |
| 18 | 2-NO$_2$ | H | 1 | H | 5 | 82 | 130–155 (amorph.) |  | −224.9 (0.5, MeOH, 25) | 1725, 1630, 1515, 1345, 1190, 900, 730 | 0.08*[4] |
| 19 | 3-NO$_2$ | H | 1 | H | 5 | 84 | 106–140 |  | −223.9 | 1720, 1630, | 0.06*[4] |
|  |  |  |  |  | 8 | 61 | (amorph.) |  | (0.5, MeOH, 25) | 1518, 1347, 1195, 925, 730 |  |
| 20 | 4-NO$_2$ | H | 1 | H | 5 | 87 | 93–123 (amorph.) |  | +130.1 (0.5, MeOH, 25) | 1720, 1625, 1507, 1345, 860, 737 | 0.21*[4] |
| 21 | 2-OCH$_3$ | H | 1 | H | 5 | 42 | 90–92.5 (amorph.) |  | +161.3 (1.2, MeOH, 24) | 1740, 1720, 1625, 1240, 1195, 1165, 1100, 1020, 760 |  |
| 22*[5] | 2-OH, 5-SO$_2$NH$_2$ | H | 1 | H | 5 | 85 | 141–150 (dec.) (amorph.) |  | +166.8 (1.0, MeOH, 26) | 1725, 1625, 1590, 1380, 1155, 925 | 0.31*[6] |

*[1]Developing solvent: AcOEt/EtOH/AcOH = 40:1:1.
*[2]Developing solvent: C$_6$H$_6$/AcOEt/EtOH/AcOH = 14:14:2:1.
*[3]Developing solvent: CHCl$_3$/EtOH/AcOH = 5:1:1.
*[4]Developing solvent: CHCl$_3$/AcOEt/AcOH = 5:7:1.
*[5]Starting material, (4R)—2-(2-hydroxy-5-sulfamoylphenyl)-4-thiazolidinecarboxylic acid: mp 200.5–202.5° C. (dec.); $[\alpha]_D^{24}$ −198.3° (c = 1.0, DMSO); IR (nujol) 3320, 3230, 1610, 1590, 1333, 1155 cm$^{-1}$.
*[6]Developing solvent: CHCl$_3$/MeOH/AcOH = 3:1:1.

TABLE II

Symmetrical Disulfides

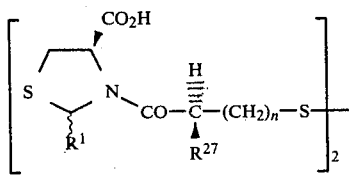

Compd. No. 23-26

| Compd. No. | $R^1$ | $R^{27}$ | n | Method of prepn. (Examp. No.) | Yield (%) | mp (°C.) | Recrystn. solvent | $[\alpha]_D$ deg. (c, solv., °C.) | IR (nujol, cm$^{-1}$) | Rf value (SiO$_2$) (corresponding thiol) |
|---|---|---|---|---|---|---|---|---|---|---|
| 23 | cyclohexyl | CH$_3$ | 1 | 1 | 95 | 106-109 | | -128.0 | 1735, 1610 | 0.37*1 |
|    |            |        |   | 4 | 76 | (amorph.) | | (0.7, MeOH, 26) | | (0.47) |
| 24 | naphthyl | CH$_3$ | 1 | 1 | 44 | 161-165 | EtOH—H$_2$O | -227.0 | 1735, 1650, | 0.26*1 |
|    |          |        |   | 5 | 47 |         |             | (0.5, MeOH, 26) | 1615, 785 | (0.40) |
| 25 | furyl | CH$_3$ | 1 | 1 | 67 | 94-105 | | -32.7 | 1737, 1620, | 0.20*2 |
|    |       |        |   | 6 | 39 | (amorph.) | | (0.5, MeOH, 25) | 1181, 1013 | (0.62) |
| 26 | thienyl | H | 1 | 1 | 43 | 84-93 | | +123.7 | 1725, 1610, | 0.31*2 |
|    |         |   |   | 5 | 41 | (amorph.) | | (1.0, MeOH, 26) | 1185 | (0.50) |

*¹Developing solvent: C$_6$H$_6$/AcOEt/EtOH/AcOH = 14:14:2:1.
*²Developing solvent: AcOEt/EtOH/AcOH = 40:1:1.

TABLE III

Symmetrical Disulfides

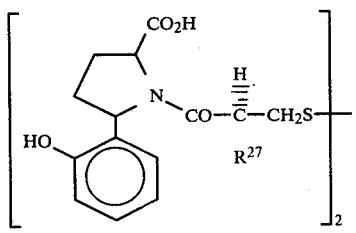

Compd. No. 27-29

| Compd. No. | $R^{27}$ | Method of prepn. (Examp. No.) | Yield (%) | mp (°C.) | Recrystn. solvent | $[\alpha]_D$ deg. (c, solv., °C.) | IR (nujol, cm$^{-1}$) | Rf value (SiO$_2$) (corresponding thiol) |
|---|---|---|---|---|---|---|---|---|
| 27*1 | H | 1 | 98 | 224.5-225.5 (dec.) | MeOH—H$_2$O | +37.5 (0.5, MeOH, 25) | 1715, 1625, 1600, 1285, 1160, 1095, 940, 770 | 0.28*4 (0.58) |
| 28*2 | H | 1 | 98 | 222-223 (dec.) | MeOH—H$_2$O | -37.5 (0.6, MeOH, 25) | 1715, 1625, 1600, 1285, 1160, 1095, 940, 770 | 0.28*4 (0.58) |
| 29*3 | CH$_3$ | 1 | 97 | 203-210 (dec.) (amorph.) | | -60.4 (1.0, MeOH, 24) | 3300, 1715, 1620, 1600, | 0.32*5 (0.54) |

TABLE III-continued
Symmetrical Disulfides

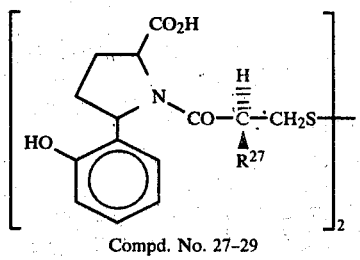

Compd. No. 27-29

| Compd. No. | $R^{27}$ | Method of prepn. (Examp. No.) | Yield (%) | mp (°C.) | Recrystn. solvent | $[\alpha]_D$ deg. (c, solv., °C.) | IR (nujol, cm$^{-1}$) | Rf value (SiO$_2$) (corresponding thiol) |
|---|---|---|---|---|---|---|---|---|
| | | | | | | | 720 | |

*[1] Starting material, α-(+)-5-(2-hydroxyphenyl)-1-(3-mercaptopropanoyl)-2-pyrrolidinecarboxylic acid: mp 197–198° C. (dec.); $[\alpha]_D^{25}$ +34.7° (c = 0.5, MeOH); IR (nujol) 3360, 1720, 1685, 1605, 1585, 1280, 1165, 760 cm$^{-1}$.
*[2] Starting material, α-(−)-5-(2-hydroxyphenyl)-1-(3-mercaptopropanoyl)-2-pyrrolidinecarboxylic acid: mp 198–199° C. (dec.); $[\alpha]_D^{25}$ −35.3° (c = 0.5, MeOH); IR (nujol) 3360, 1720, 1685, 1605, 1585, 1280, 1165, 760 cm$^{-1}$.
*[3] Starting material, α-5-(2-hydroxyphenyl)-1-[(2S)-3-mercapto-2-methylpropanoyl]-2-pyrrolidinecarboxylic acid: mp 241–242° C.; $[\alpha]_D^{25}$ −22.0° (c = 1.0, MeOH); IR (nujol) 3310, 1720, 1613, 1599, 1460 cm$^{-1}$.
*[4] Developing solvent: CHCl$_3$/AcOEt/AcOH = 5:7:1.
*[5] Developing solvent: AcOEt/EtOH/AcOH = 40:1:1.

TABLE IV

Mixed Disulfides

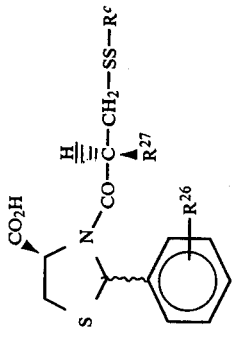

Compd. No. 30-42

| Compd. No. | $R^c$ | $R^{26}$ | $R^{27}$ | Method of prepn. (Examp. No.) | Yield (%) | mp (°C.) | Recrystn. solvent | $[\alpha]_D$ deg. (c, solv., °C.) | IR (nujol, cm$^{-1}$) | Rf value (SiO$_2$) (corresponding thiol) |
|---|---|---|---|---|---|---|---|---|---|---|
| 30 | CH$_3$ | 2-OH | H | 9<br>10 | 51<br>38 | 92-94 | AcOEt | +119.5<br>(1.0, MeOH, 25) | 3320, 1738,<br>1685, 1625,<br>1590, 1280,<br>1230, 755 | 0.48*1<br>(0.43) |
| 31 | C$_2$H$_5$ | 2-OH | H | 9<br>10<br>11 | 46<br>31<br>47 | oil | | +134.2<br>(0.5, MeOH, 24) | (neat) 1725,<br>1621, 1415,<br>1283, 1236,<br>1093, 853,<br>760 | 0.56*1<br>(0.43) |
| 32 | C$_2$H$_5$ | 2-OH, 5-Cl | CH$_3$ | 9<br>10 | 40<br>29 | oil | | +93.8<br>(0.3, MeOH, 24) | (neat) 1720,<br>1620, 1424,<br>1110, 824 | 0.56*1<br>(0.49) |
| 33 | n-C$_3$H$_7$ | H | H | 9<br>11 | 67<br>45 | 98-100 | ether | +88.9<br>(0.6, MeOH, 24) | 1743; 1617,<br>1407, 1299,<br>1230, 1202,<br>1032, 733 | 0.73*1<br>(0.70) |
| 34 | n-C$_3$H$_7$ | 2-OH | H | 9 | 31 | 65-80<br>(amorph.) | | +127.6<br>(0.5, MeOH, 25) | 1720, 1625,<br>1230, 760 | 0.51*1<br>(0.43) |
| 35 | n-C$_3$H$_7$ | 2-OH, 3-OCH$_3$ | H | 9<br>11 | 58<br>35 | oil | | +79.9<br>(0.5, MeOH, 25) | (neat) 1740,<br>1655, 1610,<br>1270, 1220,<br>760 | 0.61*1<br>(0.51) |
| 36 | n-C$_8$H$_{17}$ | 2-OH | H | 9<br>11 | 29<br>26 | oil | | +93.8<br>(0.5, MeOH, 24) | (neat) 1722,<br>1625, 1602,<br>1416, 1284,<br>1232, 1093,<br>854, 762 | 0.61*1<br>(0.43) |
| 37 | CH$_2$CH=CH$_2$ | 4-OCH$_3$ | CH$_3$ | 9 | 40 | 78-80 | | +24.4<br>(0.3, MeOH, 24) | 1750, 1647,<br>1612, 1247,<br>1176, 1033,<br>847 | 0.65*1<br>(0.63) |

TABLE IV-continued

Mixed Disulfides

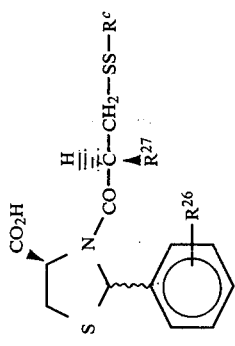

Compd. No. 30-42

| Compd. No. | $R^c$ | $R^{26}$ | $R^{27}$ | Method of prepn. (Examp. No.) | Yield (%) | mp (°C.) | Recrystn. solvent | $[\alpha]_D$ deg. (c, solv., °C.) | IR (nujol, cm$^{-1}$) | Rf value (SiO$_2$) (corresponding thiol) |
|---|---|---|---|---|---|---|---|---|---|---|
| 38 | CH$_2$CH=CH$_2$ | 2-OH | H | 9 | 60 | 60-62 | ether | +132.0 (0.5, MeOH, 24) | 1723, 1622, 1600, 1283, 1230, 1094, 920, 762 | 0.59*[1] (0.43) |
| 39 | ![tetrahydrofuran-CH2] | 2-OH | H | 9 | 22 | 168-168.5 (dec.) | EtOH—AcOEt | +133.9 (1.0, MeOH, 26) | 3240, 1745, 1620, 1600, 1380, 1240, 1030, 770 | 0.50*[1] (0.43) |
| 40 | HO$_2$C—CH(H)—C(CH$_3$)—CONH—CH$_2$—S | 2-OH | H | 12 13 | 14 12 | 84-100 (amorph.) | | +12.6 (0.5, MeOH, 23) | 3300, 1720, 1617, 1600, 1280, 1230, 760 | 0.56*[2] (0.64)*[4] (0.70)*[5] |
| 41 | (CH$_2$)$_2$CO$_2$H | 2-OH | H | 14 | 6 | 150.5-151.5 (dec.) | AcOEt—CHCl$_3$ | +83.8 (0.65, MeOH, 25) | 3360, 1710, 1625, | 0.36*[3] |
| 42 | (CH$_2$)$_2$CONH$_2$ | 2-OH | H | 9 | 21 | 154.5-155 (dec.) | EtOH—isopropyl ether | +78.4 (0.61, MeOH, 26) | 3440, 3180, 1710, 1615, 1595 | 0.24*[3] |

*[1]Developing solvent: CHCl$_3$/EtOH/AcOH = 10:1:1.
*[2]Developing solvent: n-BuOH/AcOH/H$_2$O = 4:1:1.
*[3]Developing solvent: CHCl$_3$/AcOEt/AcOH = 5:7:1.
*[4]Rf value of starting material, (4R)-3-[(2S)-3-mercapto-2-methylpropanoyl]-4-thiazolidinecarboxylic acid.
*[5]Rf value of starting material, compound 1.

TABLE V

Mixed Disulfides

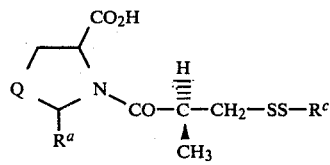

Compd. No. 43-46

| Compd. No. | $R^a$ | $R^c$ | Q | Method of prepn. (Examp. No.) | Yield (%) | mp (°C.) | Recrystn. solvent | $[\alpha]_D$ deg. (c, solv., °C.) | IR (nujol, cm$^{-1}$) | Rf value (SiO$_2$) (corresponding thiol) |
|---|---|---|---|---|---|---|---|---|---|---|
| 43*[1] | H | n-C$_3$H$_7$ | S | 9<br>10<br>11 | 87<br>79<br>82 | 95-97 | AcOEt—c-hexane | −176.2 (0.5, MeOH, 25) | 1720, 1605, 1262, 1228 | 0.56*[2] (0.47) |
| 44 | ![o-hydroxyphenyl] | n-C$_3$H$_7$ | CH$_2$ | 9<br>10<br>11 | 79<br>78<br>67 | 195-197 | AcOEt—c-hexane | −55.1 (0.5, MeOH, 25) | 1715, 1622, 1600, 1285, 1235, 775 | 0.58*[2] (0.56) |
| 45*[1] | H | CH$_2$-tetrahydrofuran | S | 9 | 17 | oil | | −151.5 (0.9, MeOH, 25) | (neat) 1735, 1645, 1610, 1285, 1230 | 0.64*[2] (0.47) |
| 46 | H | CH$_2$-tetrahydrofuran | CH$_2$ | 9 | 18 | oil | | −137.7 (0.5, MeOH, 25) | (neat) 1730, 1630, 1600, 1230 | 0.62*[2] (0.47) |

*[1] Starting material: (4R)-3-[(2S)-3-mercapto-2-methylpropanoyl]-4-thiazolidinecarboxylic acid.
*[2] Developing solvent: CHCl$_3$/EtOH/AcOH = 10:1:1.

TABLE VI

Esters

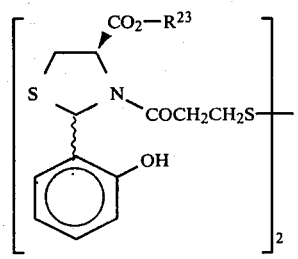

Compd. No. 47-52

| Compd. No. | $R^{23}$ | Method of prepn. (Examp. No.) | Yield (%) | mp (°C.) | Recrystn. solvent | $[\alpha]_D$ deg. (c, solv., °C.) | IR (nujol, cm$^{-1}$) |
|---|---|---|---|---|---|---|---|
| 47 | CH$_2$N-phthalimido | 17 | 81 | 105-111 | CHCl$_3$—ether | +102.1 (1.0, acetone, 25) | 3300, 1783, 1755, 1727, 1651, 1157, 729 |

TABLE VI-continued

Esters $$\left[ \begin{array}{c} \text{structure with } CO_2-R^{23}, \text{ thiazolidine ring with S, N-COCH}_2\text{CH}_2\text{S-, phenyl with OH} \end{array} \right]_2$$

Compd. No. 47–52

| Compd. No. | R[23] | Method of prepn. (Examp. No.) | Yield (%) | mp (°C.) | Recrystn. solvent | $[\alpha]_D$ deg. (c, solv., °C.) | IR (nujol, cm$^{-1}$) |
|---|---|---|---|---|---|---|---|
| 48 | CH$_2$CH$_2$N(phthalimide) | 17 | 43 | 70–76 (amorph.) | | +73.6 (0.9, acetone, 25) | 3300, 1771, 1739, 1707, 1645, 1597, 1168, 720 |
| 49 | CH$_2$OCOC(CH$_3$)$_3$ | 16 | 49 | 84–86 | C$_6$H$_6$ | +115.0 (1.1, MeOH, 27) | 3350, 1756, 1626, 1601, 1112, 993, 764 |
| 50 | CHOCOC(CH$_3$)$_3$ \| CH$_3$ | 16 | 45 | 61–65 (amorph.) | | +139.8 (0.9, MeOH, 25) | 3200, 1755, 1627, 1600, 1065, 762 |
| 51 | C$_2$H$_5$ | 15 | 68 | 195–201 | DMF—H$_2$O | +162.7 (0.5, DMF, 24) | 3340, 1745, 1625, 1600, 1255, 1230, 766 |
| 52*[1] | n-C$_4$H$_9$ | 15 | 60 | 182–184 | AcOEt— isopropyl ether | +143.7 (0.5, DMF, 24) | 3340, 1743, 1626, 1600, 1190, 1172, 763 |

*[1]Starting material, butyl (4R)-2-(2-hydroxyphenyl)-4-thiazolidinecarboxylate: mp 74–76° C.; $[\alpha]_D^{25}$ −96.5° (c = 1.0, MeOH).

TABLE VII

Esters $$\left[ \begin{array}{c} Q\text{-thiazolidine-CO}_2\text{CH}_2\text{OCOC(CH}_3)_3, \text{N-CO-C(}\equiv\text{)-CH}_2\text{-S-, CH}_3 \end{array} \right]_2$$

Compd. No. 53–54

| Compd. No. | Q | Method of prepn. (Examp. No.) | Yield (%) | mp (°C.) | Recrystn. solvent | $[\alpha]_D$ deg. (c, solv., °C.) | IR (nujol, cm$^{-1}$) |
|---|---|---|---|---|---|---|---|
| 53 | S | 16 | 48 | 93–94 | AcOEt— c-hexane | −214.0 (0.9, MeOH, 25) | 1753, 1662, 1633, 1102, 990 |
| 54 | CH$_2$ | 16 | 58 | 86–87 | isopropyl ether | −216.7 (1.0, MeOH, 25) | 1748, 1627, 1160, 1130, 1115, 990 |

TABLE VIII

Elementary Analysis of the Disulfides

| Compd. No. | Formula | Analysis (%) Calcd. (Found) | | |
|---|---|---|---|---|
| | | C | H | N |
| 1 | $C_{26}H_{28}N_2O_8S_4$ | 49.99 (50.10) | 4.52 (4.52) | 4.48 (4.54) |
| 2 | $C_{28}H_{32}N_2O_8S_4 \cdot 3/2H_2O$ | 49.47 (49.75) | 5.19 (5.01) | 4.12 (4.15) |
| 15 | $C_{24}H_{24}N_2O_8S_4 \cdot 3H_2O$ | 44.30 (44.09) | 4.65 (4.83) | 4.30 (4.20) |
| 27 | $C_{28}H_{32}N_2O_8S_2$ | 57.13 (57.02) | 5.48 (5.54) | 4.76 (4.77) |
| 28 | $C_{28}H_{32}N_2O_8S_2$ | 57.13 (56.91) | 5.48 (5.54) | 4.76 (4.71) |
| 30 | $C_{14}H_{17}NO_4S_3 \cdot C_4H_8O_2$*[1] | 48.30 (48.46) | 5.63 (5.62) | 3.13 (3.12) |
| 39 | $C_{18}H_{23}NO_5S_3$ | 50.33 (50.39) | 5.40 (5.41) | 3.26 (3.32) |
| 41 | $C_{16}H_{19}NO_6S_3$ | 46.02 (45.89) | 4.60 (4.59) | 3.36 (3.33) |
| 42 | $C_{16}H_{20}N_2O_5S_3$ | 46.13 (46.06) | 4.85 (4.85) | 6.73 (6.67) |
| 43 | $C_{11}H_{19}NO_3S_3$ | 42.69 (42.80) | 6.19 (6.16) | 4.53 (4.58) |
| 47 | $C_{45}H_{40}N_4O_{12}S_4$ | 56.47 (56.35) | 4.21 (4.33) | 5.85 (5.90) |
| 49 | $C_{38}H_{48}N_2O_{12}S_4$ | 53.50 (53.65) | 5.67 (5.68) | 3.28 (3.22) |
| 51 | $C_{30}H_{36}N_2O_8S_4$ | 52.92 (52.55) | 5.33 (5.35) | 4.11 (4.33) |
| 52 | $C_{34}H_{44}N_2O_8S_4$ | 55.41 (55.26) | 6.02 (6.03) | 3.80 (3.73) |
| 54 | $C_{30}H_{48}N_2O_{10}S_2$ | 54.53 (54.46) | 7.32 (7.32) | 4.24 (4.33) |

*[1] $C_4H_8O_2$ is ethyl acetate.

TABLE IX

NMR Spectral Data of the Disulfides

| Compd. No. | Chemical Shifts (ppm from tetramethylsilane) |
|---|---|
| 1*[1] | 2.60 (6H, m), 3.30 (4H, m), 4.63 (2H, dd, J=6 and 8Hz), 6.33 (2H, s), 6.80 (6H, m), 7.80 (2H, m), 8.50–10.50 (4H, br) |
| 3*[1] | 2.30 (6H, s), 2.70 (8H, m), 3.40 (4H, m), 4.70 (2H, dd, J=6 and 8Hz), 6.33 (2H, s), 7.17 (6H, m), 8.00 (2H, m), 8.50–10.50 (2H, br) |
| 21*[2] | 2.33–3.03 (8H, m), 3.07–3.50 (4H, m), 3.83 (6H, s), 4.88 (2H, t, J=8Hz), 6.33 (2H, s), 6.67–7.17 (6H, m), 7.70–8.00 (2H, m), 8.58 (2H, s) |
| 30*[2] | 2.25 (3H, s), 2.47–3.03 (4H, m), 3.17–3.50 (2H, m), 5.02 (1H, t, J=6Hz), 6.38 (1H, ), 6.67–7.10 (3H, m), 7.47–7.67 (1H, m), 8.08 (2H, br s) |
| 37*[2] | 0.82 (1H, d, J=5Hz), 2.43–3.13 (3H, m), 3.20–3.50 (4H, m), 3.78 (3H, s), 4.90–5.37 (3H, m), 5.43–6.15 (1H, m), 6.30 (1H, s), 6.87, 7.44 (4H, $A_2B_2$ type, each d, J=8Hz) |
| 41*[1] | 2.60–2.99 (8H, m), 3.15–3.20 (2H, m), 4.61 (1H, t, J=8Hz), 6.31 (1H, s), 6.60–7.20 (3H, m), 7.83 (1H, d, J=7Hz), 9.56 (1H, br s), 12.50 (2H, br s) |
| 48*[1] | 2.57 (4H, m), 3.30 (2H, m), 4.00 (2H, m), 4.47 (2H, m), 4.83 (1H, t, J=6.3Hz), 6.37 (1H, s), 6.80–7.70 (9H, m) |
| 50*[1] | 1.20 (9H, s), 1.53 (3H, d, J=6Hz), 2.57 (4H, m), 3.27 (2H, m), 4.93 (1H, t, J=6.3Hz), 6.40 (1H, s), 6.87–7.82 (5H, m), 7.72 (1H, br s) |

*[1] Measured in $CDCl_3$.
*[2] Measured in DMSO—$d_6$.

PHARMACOLOGICAL TEST 1

As recently it has been clear that the compounds inhibiting angiotensin I-converting enzyme may be the curative potency against both renal hypertension and essential hypertension, the compounds [I] of this invention are evaluated as antihypertensive agents by the following method.

(Method)

Male Wistar strain rats weighing 200–300 g were used. Under ether anesthesia, polyethylene cannulae are inserted into carotid artery and jugular vein. The cannula to carotid artery is connected to an electric transducer, while the cannula to jugular vein is connected to an apparatus for continuous infusion. After the complete recovery from anesthesia, angiotensin I is infused intravenously in a dose of 300 ng/kg by the apparatus for continuous infusion, and the pressor response is recorded by polygraph (Nihon Koden, RM-150). The compounds of this invention suspended in 0.5% tragacanth solution are administered orally in a dose of 0.3 ml per 100 g of body weight, and the pressor response to angiotensin I infused intravenously is measured with time. The inhibitory activity of the compounds against angiotensin I-converting enzyme is expressed as the percent inhibition of pressor response to angiotensin I. Table X shows the changes of percent inhibition of the compounds of this invention with time.

(Results)

Table X shows the results of the pharmacological tests when the compounds [I] of this invention and salts thereof are used as antihypertensive agents.

The compounds as well as the known antihypertensive mercaptoacylamino acids suppress the pressor response to angiotensin I by administered orally to unanesthesized rats, the mechanism of which is derived from inhibiting angiotensin I-converting enzyme. The compounds of this invention are derivatives of mercaptoacylamino acid, and with the comparative result in the suppressive effect on pressor response to angiotensin I by administering these compounds orally it has been proved that the compounds of this invention are well absorbed from the gastroenteric wall, and hydrolyzed gradually at the part to be shown the activity so that they have the advantages as antihypertensive agent such as long-lasting effect.

TABLE X

Suppressive Effect of the Disulfides on the Pressor Response to Angiotensin I

| Compd. No. | Dose (mg/kg) | Inhibition (%) | | |
|---|---|---|---|---|
| | | 25 | 65 | (min.) |
| 1 | 1.0 | 45 | 55 | |
| 1A*[1] | 1.0 | 55 | 35 | |
| 2 | 1.4 | 30 | 35 | |
| 2A*[2] | 1.4 | 40 | 30 | |
| 3 | 1.0 | 15 | 55 | |
| 27 | 1.3 | 65 | 55 | |
| 27A*[3] | 1.3 | 70 | 50 | |
| 34 | 1.0 | 45 | 55 | |
| 41 | 1.3 | 50 | 60 | |
| 43 | 1.0 | 70 | 40 | |

TABLE X-continued

Suppressive Effect of the Disulfides on the Pressor Response to Angiotensin I

| Compd. No. | Dose (mg/kg) | Inhibition (%) 25 | 65 | (min.) |
|---|---|---|---|---|
| 43A*[4] | 1.0 | 50 | 30 | |
| 37 | 1.0 | 60 | 35 | |
| 37A*[3] | 1.0 | 40 | 20 | |
| 49 | 1.3 | 35 | 60 | |

*[1]Corresponding thiol: (4R)-2-(2-hydroxyphenyl)-3-(3-mercaptopropanoyl)-4-thiazolidinecarboxylic acid.
*[2]Corresponding thiol: (4R)-2-(2-hydroxyphenyl)-3-[(2S)-3-mercapto-2-methylpropanoyl]-4-thiazolidinecarboxylic acid.
*[3]Corresponding thiol: α-(+)-5-(2-hydroxyphenyl)-1-(3-mercaptopropanoyl)-2-pyrrolidinecarboxylic acid.
*[4]Corresponding thiol: (4R)-3-[(2S)-3-mercapto-2-methyl-propanoyl]-4-thiazolidinecarboxylic acid.
*[5]Corresponding thiol: (4R)-3-[(2S)-3-mercapto-2-methyl-propanoyl]-2-(4-methoxyphenyl)-4-thiazolidinecarboxylic acid.

PHARMACOLOGICAL TEST 2

It has been known that aldose reductase participates in diabetic cataract which is one of the diabetic complications and that the appearance is retarded or depressed by inhibition of the aldose reductase [Acta Societatis Ophthalmologicas Japonicae, 80, 1362 (1976)]. The following method is used for the present test.

(Method)

Aldose reductase is purified from rat lenses according to the method of Hoyman et al. [J. Biol. Chem., 240, 877 (1965)]. Action of the compounds [I] of this invention is evaluated by measurement of optical density according to the J. H. Kinoshita's method [Invest. Ophthal., 13, 713 (1974)]. The reaction mixture for the measurement of the aldose reductase activity is 3.0 ml [0.007 M phosphate buffer solution (pH 6.2), 0.46 M lithium sulfate, $5 \times 10^{-5}$M NADPH, $4 \times 10^{-4}$M Dl-glyceraldehyde, 10U aldose reductase, $10^{-4}$ to $10^{-10}$M the compounds [I]] as total volume, and the absorbance thereof is measured at 340 nm.

(Results)

Table XI clearly shows that the compounds [I] of this invention whose concentration producing 50% inhibition of aldose reductase (IC$_{50}$) is order of $10^{-6}$ to $10^{-9}$M have a strong aldose reductase inhibition effect.

TABLE XI

Inhibitory Activity of the Disulfides against Aldose Reductase

| Compd. No. | IC$_{50}$ (M)*[1] |
|---|---|
| 1 | $9.7 \times 10^{-8}$ |
| 2 | $9.7 \times 10^{-8}$ |
| 3 | $8.7 \times 10^{-7}$ |
| 4 | $9.6 \times 10^{-8}$ |
| 7 | $2.0 \times 10^{-7}$ |
| 8 | $4.5 \times 10^{-7}$ |
| 10 | $7.3 \times 10^{-7}$ |
| 11 | $6.4 \times 10^{-7}$ |
| 15 | $3.1 \times 10^{-7}$ |
| 24 | $8.7 \times 10^{-7}$ |
| 34 | $8.6 \times 10^{-7}$ |
| 39 | $8.4 \times 10^{-7}$ |
| 41 | $2.0 \times 10^{-8}$ |
| Control*[2] | $9.0 \times 10^{-8}$ |

*[1]Molar concentration of a compound producing 50% inhibition of aldose reductase.
*[2]Quercitrin: referred to Acta Societatis Ophthalmologicae Japonicae, 80, 1369-1370 (1976).

STABILITY TEST

The stability of disulfide compounds is compared with that of mercaptoacylamino acids in the ethanol or the phosphate buffer solution (pH 7.0).

Condition for preservation: at room temperature, for 1 month.

Result: Disulfide compounds are more stable than mercaptoacylamino acids.

TOXICITY TEST

The value of acute toxicity of compound 1 is LD$_{50}$ 15,000 mg/kg.

(Experimental Animals)

The male ddy-std. strain mice (4 weeks of age, weighing 19-21 g) were placed in a breeding room of constant temperature and humidity (23±1° C., 55±5%) and fed freely pellet diet (CE-2, Clea Japan, Inc.) and water ad. libitum for a week. The mice showing the normal growth were selected for the experiment.

(Method of Administration)

Test compound is suspended in 0.5% tragacanth solution, and administered orally in a dose of 0.5 ml per 20 g B.W.

It is found in the above pharmacological tests that the compounds [I] of this invention are useful as antihypertensive agents with a long-lasting effect or drugs for therapy or prophylaxis of the diabetic complications. In case the compounds are used for reducing blood pressure, they can be given with the combination of diuretics such as hydroflumethiazide, furosemide, and bumetanide same as other antihypertensive agents. The compounds can be administered either orally or parenterally. The dosage forms are tablet, capsule, granule, powder, suppository, injection, etc. In the treatment of hypertension, these preparations can contain not only general excipients but also other antihypertensive agents such as reserpine, α-methyldopa, guanethidine, clonidine, hydralazine, etc., or β-adrenergic blocking agents such as propranolol, alprenolol, pindolol, bufetolol, bupranolol, bunitrolol, practolol, oxprenolol, indenolol, timolol, bunolol, etc.

On the other hand, in case the compounds are used for preventing or relieving diabetic complications, the dosage forms are tablet, capsule, granule, powder, suppository, injection, ophthalmic solution, ophthalmic ointment, etc. These preparations can also contain general exicipients.

The dose is adjusted depending on symptom, dosage form, etc. But, usual daily dosage is 1 to 5000 mg, preferably 10 to 1000 mg, in one or a few divided doses.

EXAMPLES OF FORMULATION

| (1) Oral drug | |
|---|---|
| (a) tablet | |
| compound 1 | 30 mg |
| lactose | 150 mg |
| crystalline cellulose | 50 mg |
| calcium carboxymethylcellulose | 7 mg |
| magnesium stearate | 3 mg |
| Total | 240 mg |
| compound 27 | 30 mg |
| lactose | 150 mg |
| crystalline cellulose | 50 mg |
| calcium carboxymethylcellulose | 7 mg |
| magnesium stearate | 3 mg |

| | |
|---|---|
| Total | 240 mg |
| compound 9 | 30 mg |
| lactose | 150 mg |
| crystalline cellulose | 50 mg |
| calcium carboxymethylcellulose | 7 mg |
| magnesium stearate | 3 mg |
| Total | 240 mg |
| compound 2 | 150 mg |
| lactose | 60 mg |
| crystalline cellulose | 30 mg |
| calcium carboxymethylcellulose | 7 mg |
| magnesium stearate | 3 mg |
| Total | 250 mg |
| compound 43 | 150 mg |
| lactose | 60 mg |
| crystalline cellulose | 30 mg |
| calcium carboxymethylcellulose | 7 mg |
| magnesium stearate | 3 mg |
| Total | 250 mg |
| compound 7 | 150 mg |
| lactose | 60 mg |
| crystalline cellulose | 30 mg |
| calcium carboxymethylcellulose | 7 mg |
| magnesium stearate | 3 mg |
| Total | 250 mg |

The tablets may be treated with common film-coating and further with sugar-coating.

(b) granule

| | |
|---|---|
| compound 37 | 30 mg |
| polyvinylpyrrolidone | 25 mg |
| lactose | 385 mg |
| hydroxypropylcellulose | 50 mg |
| talc | 10 mg |
| Total | 500 mg |
| compound 1 | 30 mg |
| polyvinylpyrrolidone | 25 mg |
| lactose | 385 mg |
| hydroxypropylcellulose | 50 mg |
| talc | 10 mg |
| Total | 500 mg |
| compound 9 | 30 mg |
| polyvinylpyrrolidone | 25 mg |
| lactose | 385 mg |
| hydroxypropylcellulose | 50 mg |
| talc | 10 mg |
| Total | 500 mg |

(c) powder

| | |
|---|---|
| compound 49 | 30 mg |
| lactose | 500 mg |
| starch | 440 mg |
| colloidal silica | 30 mg |
| Total | 1000 mg |
| compound 27 | 30 mg |
| lactose | 500 mg |
| starch | 440 mg |
| colloidal silica | 30 mg |
| Total | 1000 mg |
| compound 9 | 300 mg |
| lactose | 230 mg |
| starch | 440 mg |
| colloidal silica | 30 mg |
| Total | 1000 mg |
| compound 1 | 300 mg |
| lactose | 230 mg |
| starch | 440 mg |
| colloidal silica | 30 mg |
| Total | 1000 mg |

(d) capsule

| | |
|---|---|
| compound 27 | 30 mg |
| lactose | 102 mg |
| crystalline cellulose | 56 mg |
| colloidal silica | 2 mg |
| Total | 190 mg |
| compound 43 | 30 mg |
| lactose | 102 mg |
| crystalline cellulose | 56 mg |
| colloidal silica | 2 mg |
| Total | 190 mg |
| compound 1 | 30 mg |

| | |
|---|---|
| glycerin | 349.98 mg |
| butyl p-hydroxybenzoate | 0.02 mg |
| Total | 380 mg |
| compound 9 | 30 mg |
| glycerin | 349.98 mg |
| butyl p-hydroxybenzoate | 0.02 mg |
| Total | 380 mg |
| compound 2 | 200 mg |
| glycerin | 179.98 mg |
| butyl p-hydroxybenzoate | 0.02 mg |
| Total | 380 mg |

(2) Injection 1 to 30 mg of compound 6 is contained in 1 ml of the aqueous solution (pH 6.5–7.0).

(3) Ophthalmic solution

The following composition is contained in 5 ml of the aqueous solution (pH 6.0).

| | |
|---|---|
| compound 9 | 50 mg |
| propyl p-hydroxybenzoate | 0.7 mg |
| methyl p-hydroxybenzoate | 1.3 mg |
| sodium hydroxide | proper quantity |

(4) Ophthalmic ointment

The following composition is contained in 1 g.

| | |
|---|---|
| compound 2 | 20 mg |
| white petrolatum | 889.8 mg |
| mineral oil | 100 mg |
| butyl p-hydroxybenzoate | 0.2 mg |

(5) Suppository

The following composition is contained in 1 g.

| | |
|---|---|
| compound 1 | 50 mg |
| polyethylene glycol 1000 | 800 mg |
| polyethylene glycol 4000 | 150 mg |

What we claim is:

1. A compound of the formula

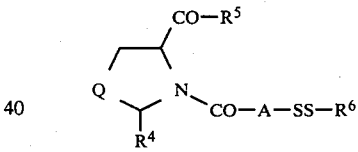

wherein
Q is methylene;
A is alkylene having 1 to 3 carbon atoms;
$R^4$ is phenyl, substituted phenyl wherein the substituent is lower alkyl, hydroxy, alkoxy, lower alkanoyloxy, benzoyloxy or benzyloxycarbonyloxy;
$R^5$ is hydroxy, lower alkoxy, amino, phenoxy, substituted lower alkoxy wherein the substituent is phthalimido or lower alkanoyloxy;
$R^6$ is alkyl having 1 to 10 carbon atoms, lower alkenyl, tetrahydrofuryl-lower alkyl,

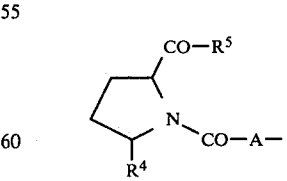

or substituted lower alkyl wherein the substituents are 1 to 2 groups independently selected from carboxy, carbamoyl, amino, lower alkanoylamino, benzoylamino and benzyloxycarbonylamino.

2. A compound of the formula

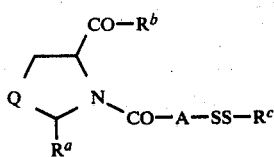

wherein
Q is methylene;
$R^a$ is lower alkyl;
$R^b$ is $R^{14}$, or $R^{17}$;
$R^c$ is $R^{15}$, or $R^{18}$;
and when
$R^b$ is $R^{14}$, $R^c$ is $R^{15}$; and when $R^b$ is $R^{17}$, $R^c$ is $R^{18}$;
A is alkylene having 1 to 3 carbon atoms;
$R^{14}$ is hydroxy, amino or lower alkoxy;
$R^{15}$ is alkyl having 8 to 10 carbon atoms, lower alkenyl, tetrahydrofuryl-lower alkyl, phenyl-lower alkyl, substituted lower alkyl wherein the substituent is carboxy or carbamoyl;
$R^{17}$ is phenoxy or substituted lower alkoxy wherein the substituent is hydroxy, succinimido, maleimido, phthalimido or lower alkanoyloxy;
$R^{18}$ is alkyl having 1 to 10 carbon atoms, lower alkenyl, tetrahydrofuryl-lower alkyl or

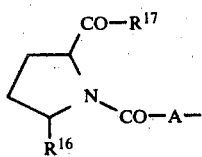

$R^{16}$ is hydrogen or lower alkyl.

3. A compound as claimed in claim 1, wherein A is —CH$_2$—, —CH(CH$_3$)—, —(CH$_2$)$_2$—, —CH(CH$_3$)CH$_2$— or —(CH$_2$)$_3$—.

4. A compound as claimed in claim 1, wherein
$R^4$ is phenyl, 2-hydroxyphenyl, 4-hydroxyphenyl or 2-acetoxyphenyl;
$R^5$ is hydroxy or pivaloyloxymethoxy;
$R^6$ is n-propyl, allyl, tetrahydrofuryl or

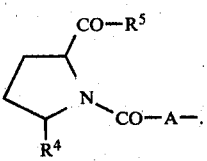

5. A compound as claimed in claim 2, wherein
$R^{14}$ is hydroxy or ethoxy;
$R^{15}$ is n-octyl, allyl or tetrahydrofurfuryl.

6. A compound as claimed in claim 2, wherein
$R^{17}$ is pivaloyloxymethoxy or 2-phthalimidoethoxy;
$R^{18}$ is tetrahydrofurfuryl or

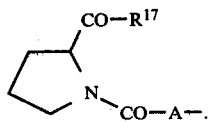

7. 1,1'-[3,3'-Dithiobis(propanoyl)]bis[5-(2-hydroxyphenyl)-2-pyrrolidinecarboxylic acid] of the formula in claim 1.

8. 1,1'-[3,3'-Dithiobis[(2S)-2-methylpropanoyl]]bis[5-(2-hydroxyphenyl)-2-pyrrolidinecarboxylic acid] of the formula in claim 1.

9. 5-(2-Hydroxyphenyl)-1-[(2S)-2-methyl-3-propyldisulfanylpropanoyl]-2-pyrrolidinecarboxylic acid of the formula in claim 1.

10. (2S)-1-[(2S)-2-Methyl-3-[(tetrahydrofurfuryl)-disulfanyl]propanoyl]proline.

11. A pharmaceutical composition for treating a person having high blood pressure comprising a compound as claimed in claim 1 in an amount sufficient to reduce blood pressure, and at least one pharmaceutically acceptable excipient.

12. A method for reducing blood pressure which comprises administering to a person having high blood pressure, a composition comprising a compound as claimed in claim 2, and at least one pharmaceutically acceptable excipient.

13. A compound as claimed in claim 1 or 2, wherein A is —(CH$_2$)$_2$—.

14. A compound as claimed in claim 1 or 2, wherein A is —CH(CH$_3$)CH$_2$—.

* * * * *

UNITED STATES PATENT AND TRADEMARK OFFICE
CERTIFICATE OF CORRECTION

PATENT NO. : 4,410,542

DATED : October 18, 1983

INVENTOR(S) : Jun-ichi IWAO et al

It is certified that error appears in the above-identified patent and that said Letters Patent is hereby corrected as shown below:

Column 11, line 24: "$D^{25}$" should be --$D^{23}$--.

Columns 21 and 22, third line from bottom of page: "$D^{24}$" should be --$D^{26}$--.

Column 35, Table IX: first line under heading "Chemical Shifts...", after "2.60", "(6H" should be --(8H--.

Column 42, line 41, Claim 12: after "claim", "2" should be --1 or 2--.

Signed and Sealed this

Twelfth Day of June 1984

[SEAL]

Attest:

Attesting Officer

GERALD J. MOSSINGHOFF

Commissioner of Patents and Trademarks